(12) United States Patent
Schaper et al.

(10) Patent No.: US 6,592,862 B1
(45) Date of Patent: Jul. 15, 2003

(54) METHODS FOR THE MODULATION OF THE GROWTH OF COLLATERAL ARTERIES AND/OR OTHER ARTERIES FROM PREEXISTING ARTERIOLAR CONNECTIONS

(75) Inventors: Wolfgang Schaper, Bad Nauheim/Rödgen (DE); Wulf D. Ito, Lüneburg (DE)

(73) Assignee: Max-Planck-Gesellschaft zur Förderung der Wissenschaften e.V., Berlin (DE)

(*) Notice: Subject to any disclaimer, the term of this patent is extended or adjusted under 35 U.S.C. 154(b) by 0 days.

(21) Appl. No.: 09/402,358

(22) PCT Filed: Apr. 1, 1998

(86) PCT No.: PCT/EP98/01891

§ 371 (c)(1),
(2), (4) Date: Dec. 10, 1999

(87) PCT Pub. No.: WO98/44953

PCT Pub. Date: Oct. 15, 1998

(30) Foreign Application Priority Data

Apr. 4, 1997 (EP) .............................................. 97105647

(51) Int. Cl.[7] .............................................. A61K 38/19

(52) U.S. Cl. .............................. 424/85.1; 514/2; 514/8; 514/12

(58) Field of Search ........................ 424/85.1; 435/724; 514/12, 44, 2, 8

(56) References Cited

FOREIGN PATENT DOCUMENTS

WO    WO 96/26742    9/1996

OTHER PUBLICATIONS

Abe, Y., et al, "Curcumin Inhibition of Inflammatory Cytokine Production by Human Peripheral Blood Monocytes and Alveolar Macrophages," *Pharmacol. Res.* 39:41–47 (Jan. 1999).
Adams, D.H., and Lloyd, A.R., "Chemokines: leucocyte recruitment and activation cytokines," *The Lancet* 349:490–495 (Feb. 1997).
Alam, R., et al., Monocyte Chemotactic Protein–2, Monocyte Chemotactic Protein–3, and Fibroblast–Induced Cytokine, *J. Immunol.* 153:3155–3159 (Oct. 1994).
Arras, M., et al., "Macrophages Accumulate and Release Tumor Necrosis Factor–α in the Ischemic Porcine Myocardium," *Supplement to Circulation, Abstracts from the 65th Scientific Sessions* 86:1–33 (Oct. 1992).
Arras, M., et al., "Monocyte Activation in Angiogenesis and Collateral Growth in the Rabbit Hindlimb," *J. Clin. Invest.* 101:49–50 (Jan. 1998).

Boring, L., et al., "Impaired Monocyte Migration and Reduced Type 1 (Th1) Cytokine Responses in C–C Chemokine Receptor 2 Knockout Mice," *J. Clin. Invest.* 100:2552–2561 (Nov. 1997).
Bright, C., et al., "Identification of a Non Peptidic Rantes Antagonist," *Bioorg. Med. Chem. Letts.* 8:771–774 (Apr. 1998).
Bustos, C., et al., "HMG–CoA Reductase Inhibition by Atorvastatin Reduces Neointimal Inflammation in a Rabbit Model of Atherosclerosis," *J. Am. Coll. Cardiol.* 32:2057–2064 (Dec. 1998).
Butcher, E.C., "Leukocyte–Endothelial Cell Recognition: Three (or More) Steps to Specificity and Diversity," *Cell* 67:1033–1036 (Dec. 1991).
Charo, I.F., et al., "Molecular cloning and functional expression of two monocyte chemoattractant protein 1 receptors reveals alternative splicing of the carboxyl–terminal tails," *PNAS USA* 91:2752–2756 (Mar. 1994).
Chuluyan, H.E., et al., "IL–1 activation of endothelium supports VLA–4 (CD49d/CD29)–mediated monocyte transendothelial migration to C5a, MIP–1α, RANTES, and PAF but inhibits migration to MCP–1: a regulatory role for endothelium–derived MCP–1," *J. Leukocyte Biol.* 58:71–79 (Jul. 1995).
Cushing, S.D., et al., "Minimally modified low density lipoprotein induces monocyte chemotactic protein 1 in human endothelial cells and smooth muscle cells," *PNAS USA* 87:5134–5138 (Jul. 1990).
Dahinden, C.A., et al., "Monocyte Chemotactic Protein 3 Is a Most Effective Basophil– and Eosinophil–activating Chemokine," *J. Exp. Med.* 179:751–756 (Feb. 1994).

(List continued on next page.)

*Primary Examiner*—Prema Mertz
(74) *Attorney, Agent, or Firm*—Sterne, Kessler, Goldstein & Fox P.L.L.C.

(57) ABSTRACT

Described is the modulation of the growth of collateral arteries and/or other arteries from preexisting arterlolar connections. Methods are provided for enhancing the growth of collateral arteries and/or other arteries from preexisting arteriolar connections comprising contacting tissue or cells with a monocyte chemotactic protein (MCP) or a nudeic acid molecule encoding said MCP. Furthermore, the use of a MCP or a nucleic acid molecule encoding said MCP for the preparation of pharmaceutical compositions for enhancing collateral growth of collateral arteries and/or other arteries from preexisting arteriolar connections is described, Also provided are methods for the treatment of tumors comprising contacting tissue or cells with an agent which suppresses the growth of collateral arteries and/or other arteries from preexisting arteriolar connections through the attraction of monocytes. Described is further the use of an agent which suppresses the growth of collateral arteries and/or other arteries from preexisting arteriolar connections through attraction of monocytes for the preparation of pharmaceutical compositions for the treatment of tumors.

14 Claims, 9 Drawing Sheets

OTHER PUBLICATIONS

Figure 1A:
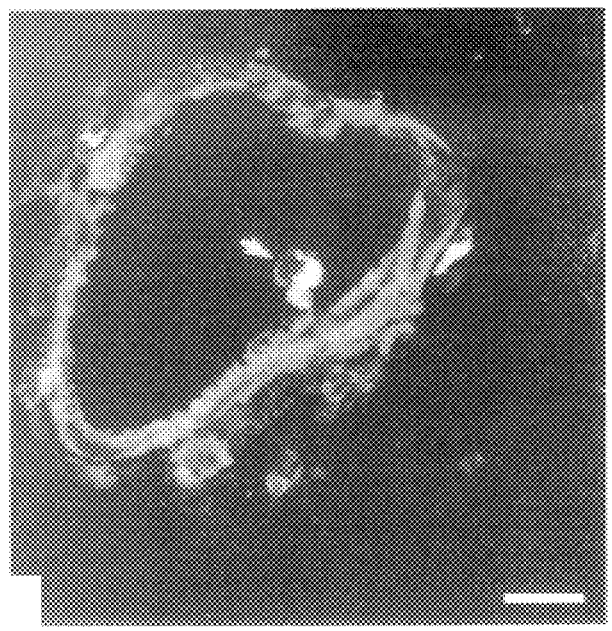
Figure 1B:
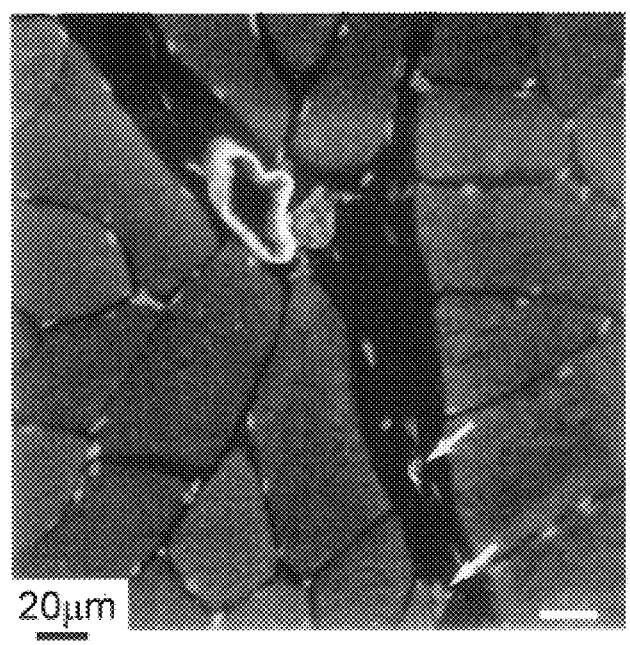

Douglas, M.S., et al., "Endothelial production of MCP–1: modulation by heparin and consequences for mononuclear cell activation," *Immunol.* 92:512–518 (Dec. 1997).

Ferrara, N., et al., "Molecular and Biological Properties of the Vascular Endothelial Growth Factor Family of Proteins," *Endocrine Rev.* 13:18–32 (Feb. 1992).

Franci, C., et al., "Monocyte Chemoattractant Protein–3, but Not Monocyte Chemoattractant Protein–2, Is a Functional Ligand of the Human Monocyte Chemoattractant Protein–1 Receptor," *J. Immunol.* 1554:6511–6517 (Jun. 1995).

Fuentes, M.E., et al., "Controlled Recruitment of Monocytes and Macrophages to Specific Organs Through Transgenic Expression of Monocyte Chemoattractant Protein–1," *J. Immunol.* 155:5769–5776 (Dec. 1995).

Furukawa, Y., et al., "Anti–Monocyte Chemoattractant Protein–1/Monocyte Chemotactic and Activating Factor Antibody Inhibits Neointimal Hyperplasia in Injured Rat Carotid Arteries," *Circ. Res.* 84:306–314(Feb. 1999).

Garcia–Zepeda, E.A., et al., "Human Monocyte Chemoattractant Protein (MCP)–4 Is a Novel CC Chemokine with Activities on Monocytes, Eosinophils, and Basophils Induced in Allergic and Nonallergic Inflammation That Signals Through the CC Chemokine Receptors (CCR)–2 and –3," *J. Immunol.* 157:5613–5626 (Dec. 1996).

Ghirnikar, R.S., et al., "Chemokine inhibition in rat stab wound brain injury using antisense oligodeoxynucleotides," *Neurosci. Letts.* 247:21–24 (May 1998).

Gibbs, J.B., and Oliff, A., "Pharmaceutical Research in Molecular Oncology," *Cell* 79:193–198 (Oct. 1994).

Gong, J.–H., and Clark–Lewis, I., "Antagonists of Monocyte Chemoattractant Protein 1 Identified by Modification of Functionally Critical $NH_2$–terminal Residues," *J. Exp. Med.* 181:631–640 (Feb. 1995).

Gong, J.–H., et al., "An Antagoinst of Monocyte Chemoattractant Protein 1 (MCP–1) Inhibits Arthritis in the MRL–1pr Mouse Model," *J. Exp. Med.* 186:131–137 (Jul. 1997).

Hernádnez–Presa, M., et al., "Angiotensin–Converting Enzyme Inhibition Prevents Arterial Nuclear Factor–kB Activation, Monocyte Chemoattractant Protein–1 Expression, and Macrophage Infiltration in a Rabbit Model of Early Accelerated Atherosclerosis," *Circ.* 95:1532–1541 (Mar. 1997).

Hollenberg, N.K., "Collateral Arterial Growth and Reactivity: Lessons from the Limb and Renal Blood Supply," in *Collateral Circulation. Heart, Brain, Kidney, Limbs*, Schaper, W., and Schaper, J., eds., Kluwer Academic Publ., Dordrecht, The Netherlands, pp. 1–15 (1993).

Hupp, T. R., et al., "Small Peptides Activate the Latent Sequence–Specific DNA Binding Function of p53," *Cell* 83:237–245 (Oct. 1995).

Ikeda, U., et al., "Monocyte chemoattractant protein 1 inhibits growth of rat vascular smooth muscle cells," *Am. J. Physiol.* 268: H1021–H1026 (Mar. 1995).

Imhof, B.A., and Dunon, D., "Leukocyte Migration and Adhesion," *Adv. Immunol.* 58:345–416 (1995).

Ito, W.D., et al., "Monocyte Chemotactic Protein–1 Increases Collateral and Peripheral Conductance After Femoral Artery Occlusion," *Circ. Res.* 80:829–837 (Jun. 1997).

Jain, R.K., et al., "Leukocyte–endothelial adhesion and angiogenesis in tumors," *Cancer and Metastasis Rev.* 15:195–204 (Jun. 1996).

Jakeman, L.B., et al., "Binding Sites for Vascular Endothelial Growth Factor Are Localized on Endothelial Cells in Adult Rat Tissues," *J. Clin. Invest.* 89:244–253 (Jan. 1992).

Kakizaki, Y., et al., "Production of monocyte chemoattractant protein–1 by bovine glomerular endothelial cells," *Kidney Intl.* 48:1866–1874 (Dec. 1995).

Kelly, R.W., et al., "The Inhibition of Synthesis of a β–Chemokine, Monocyte Chemotactic Protein–1 (MCP–1) by Progesterone," *Biochem. Biophys. Comm.* 239:557–561 (Oct. 1997).

Klagsbrun, M., and D'Amore, P. A., "Regulators of Angiogenesis," *Annu. Rev. Physiol.* 53:217–239 (1991).

Krishnaswamy, G., et al., "Multifunctional Cytokine Expression by Human Coronary Endothelium and Regulation by Monokines and Glucocorticoids," *Microvascular Res.* 55:189–200 (May 1998).

Kolattukudy, P.E., et al., "Myocarditis Induced by Targeted Expression of the MCP–1 Gene in Murine Cardiac Muscle," *Am. J. Pathol.* 152:101–111 (Jan. 1998).

Kumar, A.G., et al., "Induction of Monocyte Chemoattractant Protein–1 in the Small Veins of the Ischemic and Reperfused Canine Myocardium," *Circulation* 95:693–700 (Feb. 1997).

Kuratsu, J.–I., et al., "Production and Characterization of Human Glioma Cell–Derived Monocyte Chemotactic Factor," *J. Natl. Cancer Inst.* 81:347–351 (Mar. 1989).

Lane, T.E., et al., "Inhibition of nitric oxide synthase–2 reduces the severity of mouse hepatitis virus–induced demyelination: implications for NOS2/NO regulation of chemokine expression and inflammation," *J. NeuroVirol.* 5:48–54 (Feb. 1999).

Leonard, E.J., and Yoshimura, T., "Human monocyte chemoattractant protein–1 (MCP–1)," *Immunol. Today* 11:97–101 (Mar. 1990).

Leung, D.W., et al., "Vascular Endothelial Growth Factor Is a Secreted Angiogenic Mitogen," *Science* 246:1306–1309 (Dec. 1989).

Locati, M., et al., "Inhibition of Monocyte Chemotaxis to C–C Chemokines by Antisense Oligonucleotide for Cytosolic Phospholipase $A_2$," *J. Biol. Chem.* 271:6010–6016 (Mar. 1996).

Lusti–Narasimhan, M., et al., "Mutation of $Leu^{25}$ and $Val^{27}$ Introduces CC Chemokine Activity into Interleukin–8," *J. Biol. Chem.* 270:2716–2721 (Feb. 1995).

Marczin, N., et al., "Monocyte–Induced Downregulation of Nitric Oxide Synthase in Cultured Aortic Endothelial Cells," *Arterioscler. Thromb. Vasc. Biol.* 16:1095–1103 (Sep. 1996).

Mattfeldt, T., and Mall, G., "Dipyridamole–induced capillary endothelial cell proliferation in the rat heart—a morphometric investigation," *Cardiovas. Res.* 17:229–237 (Apr. 1983).

McFadden, G., and Kelvin, D., "New Strategies for Chemokine Inhibition and Modulation," *Biochem. Pharmacol.* 54:1271–1280 (Dec. 1997).

Millauer, B., et al., "High Affinity VEGF Binding and Developmental Expression Suggest Flk–1 as a Major Regulator of Vaculogenesis and Angiogenesis," *Cell* 72:835–846 (Mar. 1993).

Milner, J., "DNA damage, p53 and anticancer therapies," *Nature Med.* 1:879–882 (Sep. 1995).

Morrissey, J.J., and Klahr, S., "Differential effects of ACE and $AT_1$ receptor inhibition on chemoattractant and adhesion molecule synthesis," *Am. J. Physiol.: Regulatory, Integrative and Comparative Physiol.* 43:F580–F586 (Mar. 1998).

Negus, R.P.M., et al., "Hypoxia down–regulates MCP–1 expression: implications for macrophage distribution in tumors," *J. Leukocyte Biol.* 63:758–765 (Jun. 1998).

Neumann, F.–J., et al., "Induction of Cytokine Expression in Leukocytes by Binding of Thrombin–Stimulated Platelets," *Circ.* 95:2387–2394 (May 1997).

Nishio, Y., et al., "Cilostazol, a cAMP Phosphodiesterase Inhibitor, Attenuates the Production of Monocyte Chemoattractant Protein–1 in Response to Tumor Necrosis Factor–α in Vascular Endothelial Cells," *Horm. Metab. Res.* 29:491–495 (Oct. 1997).

Okada, M., et al., "Cyclic Stretch Upregulates Production of Interleukin–8 and Monocyte Chemotactic and Activating Factor/Monocyte Chemoattractant Protein–1 in Human Endothelial Cells," *Arterioscler. Thromb. Vasc. Biol.* 18:894–901 (Jun. 1998).

Oppenheim, J. J., et al., "Properties of the Novel Proinflammatory Supergene "Intercrine" Cytokine Family," *Annu. Rev. Immunol.* 9:617–648 (1991).

Paavola, C.D., et al., "Monomeric Monocyte Chemoattractant Protein–1 (MCP–1) Binds and Activates the MCP–1 Receptor CCR2B," *J. Biol. Chem.* 273:33157–33165 (Dec. 1998).

Parry, G.C.N., et al., "IL–1β–Induced Monocyte Chemoattractant Protein–1 Gene Expression in Endothelial Cells Is Blocked by Proteasome Inhibitors," *Arterioscler. Thromb. Vas. Biol.* 18:934–940 (Jun. 1998).

Paskins–Hurlburt, A.J. and Hollenberg, N.K., "'Tissue Need' and Limb Collateral Arterial Growth," *Circ. Res.* 70:546–553 (Mar. 1992).

Pasyk, S., et al., "DNA synthesis in coronary collaterals after coronary artery occlusion in conscious dog," *Am. J. Physiol.* 242:H1031–H1037 (Jun. 1982).

Penton–Rol, G., et al., "Selective Inhibition of Expression of the Chemokine Receptor CCR2 in Human Monocytes by IFN–γ," *J. Immunol.* 160:3869–3873 (Apr. 1998).

Peters, K.G., et al., "Vascular endothelial growth factor receptor expression during embryogenesis and tissue repair suggests a role in endothelial differentiation and blood vessel growth," *PNAS USA* 90:8915–8919 (Oct. 1993).

Plate, K.H., et al., "Vascular endothelial growth factor is a potential tumour angiogenesis factor in human gliomas in vivo," *Nature* 359:845–848 (Oct. 1992).

Plater–Zyberk, C., et al., "Effect of a CC chemokine receptor antagonist on collagen induced arthritis in DBA/1 mice," *Immunol. Letts.* 57:117–120 (Jun. 1997).

Porreca, E., et al., "Monocyte Chemotactic Protein 1 (MCP–1) Is a Mitogen for Cultured Rat Vascular Smooth Muscle Cells," *J. Vasc. Res.* 34:58–65 (Jan.–Feb. 1997).

Proost, P., et al., "Chemical Synthesis, Purification and Folding of the Human Monocyte Chemotactic Proteins MCP–2 and MCP–3 into Biologically Active Chemokines," *Cytokine* 7:97–104 (Feb. 1995).

Rand, M.L., et al., "Inhibition of T Cell Recruitment and Cutaneous Delayed–Type Hypersensitivity–Induced Inflammation with Antibodies to Monocyte Chemoattractant Protein–1," *Am. J. Pathol.* 148:855–864 (Mar. 1996).

Satriano, J.A., et al., "Oxygen Radicals as Second Messengers for Expression of the Monocyte Chemoattractant Protein, JE/MCP–1, and the Monocyte Colony–stimulating Factor, CSF–1, in Response to Tumor Necrosis Factor–α and Immunoglobulin G," *J. Clin. Invest.* 92:1564–1571 (Sep. 1993).

Schaper, W., and Ito, W.D., "Therapeutic targets in cardiovascular disorders," *Curr. Opin. Biotechnol.* 7:635–640 (Dec. 1996).

Seitz, M., et al., "Methotrexate Action in Rheumatoid Arthritis: Stimulation of Cytokine Inhibitor and Inhibition of Chemokine Production by Peripheral Blood Mononuclear Cells," *Brit. J. Rheumatol.* 34:602–609 (Jul. 1995).

Shyy, Y.–J., et al., "Fluid shear stress induces a biphasic response of human monocyte chemotactic protein 1 gene expression in vascular endothelium," *PNAS USA* 91:4678–4682 (May 1994).

Sica, A., et al., "Bacterial Lipolysaccharide Rapidly Inhibits Expression of C–C Chemokine Receptors in Human Monocytes," *J. Exp. Med.* 185:969–974 (Mar. 1997).

Springer, T.A., "Traffic Signals for Lymphocyte Recirculation and Leukocyte Emigration: The Multistep Paradigm," *Cell* 76:301–314 (Jan. 1994).

Springer, T.A., "Traffic Signals on Endothelium for Lymphocyte Recirculation and Leukocyte Emigration," *Annu. Rev. Physiol.* 57:827–872 (1995).

Symons, J.D., et al., "Repeated Dipyridamole Administration Enhances Collateral–Dependent Flow and Regional Function During Exercise. A Role for Adenosine," *Circ. Res.* 73:503–513 (Sep. 1993).

Tangirala, R.K., et al., "Regulation of Expression of the Human Monocyte Chemotactic Protein–1 Receptor (hCCR2) by Cytokines," *J. Biol. Chem.* 272:8050–8056 (Mar. 1997).

Tornling, C., "Capillary Neoformation in the Heart and Skeletal Muscle during Dipyridamole–Treatment and Exercise," *Acta Pathol. Microbiol. Immunol. Scand.* 278 (*Suppl.*):5–63 (1982).

Torry, R.J., et al., "Dipyridamole–induced capillary growth in normal and hypertropic hearts," *Am. J. Physiol.* 262:H980–H986 (Apr. 1992).

Tuder, R.M., et al., "Increased Gene Expression for VEGF and the VEGF Receptors KDR/Flk and Flt in Lungs Exposed to Acute or to Chronic Hypoxia," *J. Clin. Invest.* 95:1798–1807 (Apr. 1995).

Unthank, J.L., et al., "Wall Remodeling During Luminal Expansion of Mesenteric Arterial Collaterals in the Rat," *Circ. Res.* 79:1015–1023 (Nov. 1996).

van den Berg, R.H., et al., "The First Subcomponent of Complement, C1q, Triggers the Production of IL–8, IL–6, and Monocyte Chemoattractant Peptide–1 by Human Umbilical Vein Endothelial Cells," *J. Immunol.* 161:6924–6930 (Dec. 1998).

van der Velden, V.H.J., et al., "Interleukin–1β and interferon–γ differentially regulate release of monocyte chemotactic protein–1 and interleukin–β by human bronchial epithelial cells," *Eur. Cytokine Netw.* 9:269–278 (Sep. 1998).

Van Wauwe, J., et al., "The inhibitory effect of pentamidine on the production of chemotactic cytokines by in vitro stimulated human blood cells," *Inflamm. Res.* 45:357–363 (Jul. 1996).

Wang, D.L., et al., "Mechanical Strain Induces Monocyte Chemotactic Protein–1 Gene Expression in Endothelial Cells. Effects of Mechanical Strain on Monocyte Adhesion to Endothelial Cells," *Circ. Res.* 77:294–302 (Aug. 1995).

Wang, X.–C., et al., "Suppression of NF–kB–Dependent Proinflammatory Gene Expression in Human RPE Cells by a Proteasome Inhibitor," *Invest. Ophthalmol. Vis. Sci.* 40:477–486 (Feb. 1999).

Ware, J.A., and Simons, M., "Angiogenesis in ischemic heart disease," *Nature Med.* 3:158–164 (Feb. 1997).

Weber, K.S.C., et al., "Differential immobilization and hierarchical involvement of chemokines in monocyte arrest and transmigration on inflamed endothelium in shear flow," *Eur. J. Immunol.* 29:700–712 (Feb. 1999).

Wung, B.-S., et al., "Cyclical strain increases moncyte chemotactic protein–1 secretion in human endothelial cells," *Am. J. Physiol.* 270:H1462–H1468 (Apr. 1996).

Xu, Y.X., et al., "Curcumin, a compound with anti–inflammatory and anti–oxidant properties, down–regulates chemokine expression in bone marrow stromal cells," *Exp. Hematol.* 25:413–422 (May 1997).

Xu, Y.X., et al., "Curcumin Inhibits IL1α and TNF–α Induction of AP–1 and NF–kB DNA–Binding Activity in Bone Marrow Stromal Cells," *Hematopathol. Mol. Hematol.* 11:49–62 (1997–1998).

Yamada, K., et al., "Physiological Concentration of 17β–Estradiol Inhibits Chemotaxis of Human Monocytes in Response to Monocyte Chemotactic Protein 1," *Artery* 22:24–36 (1996).

Yoshimura, T., et al., "Human monocyte chemoattractant protein–1 (MCP–1)," *FEBS Letts.* 244:487–493 (Feb. 1989).

Zeiher, A.M., et al., "Nitric Oxide Modulates the Expression of Monocyte Chemoattractant Protein 1 in Cultured Human Endothelial Cells," *Circ. Res.* 76:980–986 (Jun. 1995).

Zhou, Y., et al., "LPS down–regulates the expression of chemokine receptor CCR2 in mice and abolishes macrophage infiltration in acute inflammation," *J. Leukocyte Biol.* 65:265–269 (Feb. 1999).

Zimmerman, R., et al., "Microembolization Changes Gene Expression in Porcine Hearts," *Circulation (Suppl.)* 88:I–545, Abstr. No. 2936 (Oct. 1993).

International Search Report from International Appl. No. PCT/EP98/01891, mailed Aug. 21, 1998.

Isik et al. J Surg Res 1996, vol. 61, pp. 71–76. Monocyte chemoattractant protein–1 mRNA expression in hemagiomas and vascular malformations.*

Wysocki et al. 1996. J Cell Biochem. vol. 62, pp. 303–313. Monocyte chemoattractant protein–1 gne expression in injured pig artery coincides with early appearance of infiltrating monocytes/macrophages.*

Baffour, R. et al., "Enhanced angiogenesis and growth of collaterals by in vivo administration of recombinant basic fibroblast growth factor in a rabbit model of acute lower limb ischemia: Dose–response effect of basic fibroblast growth factor," *J. Vasc. Surg.* 16:181–191, Mosby–Year Book Inc. (1992).

Lazarous, D.F. et al., "Comparative Effects of Basic Fibroblast Growth Factor and Vascular Endothelial Growth Factor on Coronary Collateral Development and the Arterial Response to Injury," *Circulation* 94:1074–1082, American Heart Association (1996).

Schaper, W., "Angiogenesis in the adult heart," *Basic Res. Cardiol.* 86(Suppl 2):51–56, Steinkopff Verlag (1991).

Schechter, J. and Weiner, R., "Changes in Basic Fibroblast Growth Factor Coincident with Estradiol–Induces Hyperplasia of the Anterior Pituitaries of Fischer 344 and Sprague–Dawley Rats," *Endocrinology* 129:2400–2408, The Endocrine Society (1991).

Unger, E.F. et al., "Basic fibroblast growth factor enhances myocardial collateral flow in a canine model," *Am. J. Physiol.* 266:H1588–H1595, American Physiological Society (1994).

Andeweg, J., "The anatomy of collateral venous flow from the brain and its value in aetiological interpretation of intracranial pathology," *Neuroradiology* 38:621–628, Springer–Verlag (Oct. 1996).

Bloor, C.M., "Discussion," *Circulation* 53(Suppl. I):I–63–I–65, American Heart Association, Inc. (1976).

Bonavida, B., et al., "Effects of platelet–activating factor on peripheral blood monocytes: induction and priming for TNF secretion," *J. Lipid Mediat.* 2:S65–S76, Elsevier Science B.V. (1990).

Buschman, I., et al., "Anti–Adhesion Monoclonal Antibodies Against ICAM Inhibit Arteriogenesis," *J. Am. Coll. Cardiol.* 33(Suppl.):318A, Abs. No. 911–1, Elsevier Biomedical Press (Feb. 1999).

Buschman, I., and Schaper, W., "The pathophysiology of the collateral circulation (arteriogenesis)," *J. Pathol.* 190:338–342, John Wiley & Sons, Ltd. (Feb. 2000).

Carmeliet, P., "Mechanisms of angiogenesis and arteriogenesis," *Nat. Med.* 6:389–395, Nature America, Inc. (Mar. 2000).

Deindl, E., et al., "Role of Ischemia and of Hypoxia–Inducible Genes in Arteriogenesis After Femoral Artery Occlusion in the Rabbit," *Circ. Res.* 89:779–786, Lippincott Williams & Wilkins (Oct. 2001).

Dosquet, C., et al., "Molecular mechanism of blood monocyte adhesion to vascular endothelial cells," *Nouv. Rev. Fr. Hematol.* 34(Suppl.):S55–S59, Springer–Verlag (1992).

Haque, N.S., et al., "CC Chemokine I–309 Is the Principal Monocyte Chemoattractant Induced by Apolipoprotein (a) in Human Vascular Endothelial Cells," *Circulation* 102:786–792, Lippincott Williams & Wilkins (Aug. 2000).

Hoefer, I., et al., "Essential role of ICAM–1 mediated monocyte migration during arteriogenesis," *Eur. Heart J.* 4(Abstr. Suppl.):499, Abs. No. 2614, European Society of Cardiology (Aug.–Sep. 2002) printed Sept. 27, 2002 from http://ex2.excerptamedica.com/o2esc/index.cfm?fuseaction=CIS2002&hoofdnav=Search& content=zk.results__all&searchtext=&topicselected=03.07&what=AUTHOR&selection=All& abstrnbr=2614.

Ma, X.–1., et al., "Coronary Endothelial and Cardiac Protective Effects of a Monoclonal Antibody to Intercellular Adhesion Molecule–1 in Myocardial Ischemia and Reperfusion," *Circulation* 86:937–946, American Heart Association, Inc. (1992).

Miller, M.D., and Krangel, M.S., "The human cytokine I–309 is a monocyte chemoattractant," *Proc. Natl. Acad. Sci.* 89:2950–2954, National Academy of Sciences (1992).

Monk, P.N., et al., "Multiple signalling pathways in the C5a–induced expression of adhesion receptor Mac–1," *Biochim. Biophys. Acta* 1221:323–329, Elsevier Science B.V. (1994).

Seekamp, A., and Ward, P.A., "Ischemia—Reperfusion Injury," *Inflammatory Disease Therapy: Preclinical and Clinical Developments*, Bonney, R.J., et al., eds. Birkhäuser Verlag, Basel, Switzerland, pp. 137–152 (1993).

Vaddi, K., and Newton, R.C., "Regulation of Monocyte Integrin Expression by β–Family Chemokines," *J. Immunol.* 153:4721–4732, The American Association of Immunologists (1994).

Wain, J.H., et al., "Leucocyte chemotaxis: Examination of mitogen–activated protein kinase and phosphoinositide 3–kinase activation by Monocyte Chemoattractant Proteins–1, –2, –3 and –4," *Clin. Exp. Immunol.* 127:436–444, Blackwell Science Ltd. (Mar. 2002).

Wong, D., and Dorovini–Zis, K., "Upregulation of intercellular adhesion molecule–1 (ICAM–1) expression in primary cultures of human brain microvessel endothelial cells by cytokines and lipopolysaccharide," *J. Neuroimmunol.* *39*:11–22, Elsevier Science B.V. (1992).

Schaper, J., et al., "The Endothelial Surface of Growing Coronary Collateral Ateries. Intimal Margination and Diapedesis of Monocytes," *Virchows Arch. A Path. Anat. Histol.* *370*:193–205 (1976).

Schaper, W., "Coronary Collateral Development: Concepts and Hypothesis," *Collateral Circulation. Heart. Brain, Kidney. Limbs,* Schaper, W., and Schaper, J., eds., Kluwer Academic Publ., Dordrecht, The Netherlands, pp. 41–64 (1993).

Schaper, W., and Ito, W.D., "Molecular Mechanisms of Coronary Collateral Vessel Growth," *Circ. Res. 79*: 911–919 (Nov. 1996).

\* cited by examiner

METHODS FOR THE MODULATION OF THE GROWTH OF COLLATERAL ARTERIES AND/OR OTHER ARTERIES FROM PREEXISTING ARTERIOLAR CONNECTIONS

The present invention relates generally to the modulation of the growth of collateral arteries or other arteries from preexisting arteriolar connections. In particular, the present invention provides a method for enhancing the growth of collateral arteries and/or other arteries from preexisting arteriolar connections comprising contacting tissue or cells with a monocyte chemotactic protein (MCP) or a nucleic acid molecule encoding said MCP. The present invention also relates to the use of an MCP or a nucleic acid molecule encoding said MCP for the preparation of pharmaceutical compositions for enhancing collateral growth of collateral arteries and/or other arteries from preexisting arteriolar connections. Furthermore, the present invention relates to a method for the treatment of tumors comprising contacting tissue or cells with an agent which suppresses the growth of collateral arteries and/or other arteries from preexisting arteriolar connections through the attraction of monocytes. The present invention further involves the use of an agent which suppresses the growth of collateral arteries and/or other arteries from preexisting arteriolar connections through the attraction of monocytes for the preparation of pharmaceutical compositions for the treatment of tumors.

In the treatment of subjects with arterial occlusive diseases most of the current treatment strategies aim at ameliorating their effects. The only curative approaches involve angioplasty (balloon dilatation) or bypassing surgery. The former carries a high risk of restenosis and can only be performed in certain arterial occlusive diseases, like ischemic heart disease. The latter is invasive and also restricted to certain kinds of arterial occlusive diseases. There is no established treatment for the enhancement of collateral growth.

Vascular growth in adult organisms proceeds via two distinct mechanisms, sprouting of capillaries (angiogenesis) and in situ enlargement of preexisting arteriolar connections into true collateral arteries[1]. Recent studies have disclosed mechanisms leading to angiogenesis with vascular endothelial growth factor (VEGF) as a major component[2-6]. This specific endothelial mitogen is upregulated by hypoxia and is able to promote vessel growth when infused into rabbit hindlimbs after femoral artery excision[7,8]. These studies however did not distinguish between capillary sprouting, a mechanism called angiogenesis, and true collateral artery growth. Whereas VEGF is only mitogenic for endothelial cells, collateral artery growth requires the proliferation of endothelial and smooth muscle cells and pronounced remodeling processes occur[1,9-12]. Furthermore mainly capillary sprouting is observed in ischemic territories for example in the pig heart or in rapidly growing tumors[1,3,13,14]. True collateral artery growth, however, is temporally and spacially dissociated from ischemia in most models studied[1,15]. Other or additional mechanisms as those described for angiogenesis in ischemic territories are therefore needed to explain collateral artery growth. From previous studies it is known that these collateral arteries grow from preexisting arteriolar connections[1].

However, while agents such as VEGF and other growth factors are presently being employed to stimulate the development of angiogenesis after arterial occlusion, such agents are not envisaged as being capable of modulating the growth of preexisting arteriolar connections into true collateral arteries.

Thus, the technical problem of the present invention is to provide pharmaceutical compositions and methods for the modulation of the growth of collateral arteries and/or other arteries from preexisting arteriolar connections.

The solution to this technical problem is achieved by providing the embodiments characterized in the claims.

Accordingly, the invention relates to a method for enhancing the growth of collateral arteries and/or other arteries from preexisting arteriolar connections comprising contacting tissue or cells with a monocyte chemotactic protein (MCP) or a nucleic acid molecule encoding said MCP.

For the purpose of the present invention the growth of arteries from preexisting arteriolar connections is also called "arteriogenesis". In particular, "arteriogenesis" is the in situ growth of arteries by proliferation of endothelial and smooth muscle cells from preexisting arteriolar connections supplying blood to ischemic tissue, tumor or sites of inflammation. These vessels largely grow outside the affected tissue but are much more important for the delivery of nutrients to the ischemic territory, the tumor or the site of inflammation than capillaries sprouting in the diseased tissue by angiogenic processes.

In the context of the present invention the term "monocyte chemotactic protein" or "MCP" refers to proteins and peptides which can act on monocytes and lead to augmentation of monocyte activation accumulation and migration[35]. Thus, according to the present invention, any MCP or other substances which are functionally equivalent to an MCP, namely which are capable of activating and attracting monocytes can be used for the purpose of the present invention. The action of the MCPs employed in the present invention may not be limited to the above-described specificity but they may also act on, for example eosinophils, lymphocyte subpopulations and/or stem cells.

In accordance with the present invention, it has been found that through the attraction of monocytes by monocyte chemotactic protein-1 (MCP-1) the growth of collateral arteries and arteriogenesis could be significantly enhanced in animals after femoral artery occlusion. Experiments performed within the scope of the present invention demonstrate that local infusion of MCP-1 increases both collateral- and peripheral conductance after femoral artery occlusion due to enhanced vessel growth by augmentation of monocyte accumulation concomitant with proliferative effects on endothelial and/or smooth muscle cells. Thus, MCPs or nucleic acid molecules encoding MCPs can be used to attract monocytes to a certain tissue or cell which in turn leads to growth of collateral arteries as well as to growth of arteries from preexisting arteriolar connections, which is needed for the cure of several occlusive diseases.

MCP-1 is a 14-kDa glycoprotein secreted by many cells, including vascular smooth muscle- and endothelial cells[29-32] and induces monocyte chemotaxis at subnanomolar concentrations[33]. MCP-1 is a potent agonist for the β chemokine receptors CCR 2 and CCR 4 which are both mainly expressed by monocytes but also have been found to be present on basophils, T- and B-lymphocytes[34]. These G-protein coupled seven-transmembrane-domain receptors lead to the activation of monocytes and increased adhesiveness of integrins, a process which finally leads to monocyte arrest on endothelial cells[35]. The MCP-1 gene shows large interspecies homologies[30] and can be induced by various cytokines (e.g. Tumor necrosis factor α) and immunoglobulin G[36]. Recently it has been shown in vitro that gene expression and protein secretion of MCP-1 are also upregulated by shear stress and cyclic strain[16-18]. These mechanical forces have recently been shown to increase monocyte chemotactic protein-1 (MCP-1) secretion in cultured human endothelial cells leading to increased monocyte adhesion[16-18]. These findings complement the observation that monocytes adhere and migrate into the vessel wall of collateral arteries after induction of coronary artery stenosis in the dog heart at a time when the proliferation index is maximally increased[19]. Furthermore, monocyte accumulation is also observed in the pig microembolization model of angiogenesis[20]. Moreover increased levels of MCP-1 mRNA were found in ischemic tissue of microembolized porcine myocardium[21] as well as in reperfused ischemic myocardium[37]. However, although there are several reports published that indicate that monocytes are involved in angiogenesis[22-24] monocytes were not believed to play a role in the development of collateral arteries and arteriogenesis[25].

The MCPs to be employed in the methods and uses of the present invention may be obtained from various sources described in the prior art; see, e.g., Proösl[69], Dahinden[70], Alam[71] and Oppenheim[72]. The potential exists, in the use of recombinant DNA technology, for the preparation of various derivatives of MCPs comprising a functional part thereof or proteins which are functionally equivalent to MCPs as described above. In this context, as used throughout this specification "functional equivalent or "functional part" of an MCP means a protein having part or all of the primary structural conformation of an MCP possessing at least the biological property of attracting monocytes. The functional part of said protein or the functionally equivalent protein may be a derivative of an MCP by way of amino acid deletion(s), substitution(s), insertion(s), addition(s) and/or replacement(s) of the amino acid sequence, for example by means of site directed mutagenesis of the underlying DNA. Recombinant DNA technology is well known to those skilled in the art and described, for example, in Sambrook et al. (Molecular cloning; A Laboratory Manual, Second Edition, Cold Spring Harbour Laboratory Press, Cold Spring Harbour N.Y. (1989)). For example, it was found that a mutation of the amino acids Leu25 and Val27 into Tyr introduces a novel monocyte chemoattractant activity into interleukin-8, which normally does not activate monocytes[66].

MCPs or functional parts thereof or proteins which are functionally equivalent to MCPs, may be produced by known conventional chemical syntheses or recombinant techniques employing the amino acid and DNA sequences described in the prior art[69-72], for example, MCPs may be produced by culturing a suitable cell or cell line which has been transformed with a DNA sequence encoding upon expression under the control of regulatory sequences an MCP or a functional part thereof or a protein which is functionally equivalent to MCP. Suitable techniques for the production of recombinant proteins are described in, e.g., Sambrook, supra. Methods for constructing MCPs and proteins as described above useful in the methods and uses of the present invention by chemical synthetic means are also known to those of skill in the art.

In another embodiment, the invention relates to the use of a monocyte chemotactic protein (MCP) or a nucleic acid molecule encoding said MCP for the preparation of a pharmaceutical composition for enhancing collateral growth of collateral arteries and/or other arteries from preexisting arteriolar connections.

The pharmaceutical composition comprises at least one MCP as defined above, and optionally a pharmaceutically acceptable carrier or exipient. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by conventional methods. The pharmaceutical compositions can be administered to the subject at a suitable dose. The dosage regimen may be determined by the attending physician considering the condition of the patient, the severity of the disease and other clinical factors. Administration of the suitable compositions may be effected by different ways, e.g. by intravenous, intraperetoneal, subcutaneous, intramuscular, topical or intradermal administration.

In a preferred embodiment, said MCP used in the methods and uses of the invention is selected from the group consisting of MCP-1, MCP-2, MCP-3, MCP-4, MIP-1α, RANTES, I-309 or any other CC-chemokine or classical chemoattractants like N-farnesyl peptides, C5a, leukotriene B4 or Platelet-activating factor (PAF)[35,48].

In a particularly preferred embodiment, the method and uses of the invention are for the treatment of subjects suffering from occlusive disease, preferably-selected from the group consisting of coronary artery diseases, cerebral occlusive diseases, peripheral occlusive diseases, visceral occlusive diseases, renal artery disease and mesenterial arterial insufficiency.

In a further preferred embodiment, the methods and uses of the invention are for the treatment of subjects during or after exposure to an agent or radiation or surgical treatment which damage or destroy arteries.

In a preferred embodiment, the MCP used in the methods and uses of the invention is a recombinant MCP. DNA sequences encoding MCPs which can be used in the methods and uses of the invention are described in the prior art, e.g., Garcia-Zepeda[34]. Moreover, DNA and amino acid sequences of MCPs are available in the Gene Bank database. As described above, methods for the production of recombinant proteins are well-known to the person skilled in the art; see, e.g., Sambrook, supra.

In a further preferred embodiment, the pharmaceutical composition is designed for administration in conjugation with growth factors, preferably fibroblast growth factor or vascular endothelial growth factor (VEGF). This embodiment is particularly suited for enhancing of both sprouting of capillaries (angiogenesis) and in situ enlargement of preexisting arteriolar connections into true collateral arteries. Pharmaceutical compositions comprising, for example, an MCP such as MCP-1, and a growth factor such as VEGF may be used for the treatment of peripheral vascular diseases or coronary artery disease.

In another preferred embodiment, the method of the invention comprises
(a) obtaining cells from a subject;
(b) introducing a nucleic acid molecule encoding the MCP into said cells, thereby conferring expression and secretion of the MCP in a form suitable for the attraction of monocytes; and
(c) reintroducing the cells obtained in step (b) into the subject.

It is envisaged by the present invention that the MCPs and the nucleic acid molecules encoding the MCPs are administered either alone or in combination, and optionally together with a pharmaceutically acceptable carrier or exipient. Said nucleic acid molecules may be stably integrated into the genome of the cell or may be maintained in a form extrachromosomally. On the other hand, viral vectors may be used for transfecting certain cells or tissues, preferably cells and tissue surrounding preexisting arteriolar connections. Elements capable of targeting a nucleic acid molecule and/or protein to specific cells are described in the prior art, for example Somia, Proc. Natl. Acad. Sci., USA 92 (1995), 7570–7574. Thus, it is possible to employ the methods and uses of the invention for somatic gene therapy, which is based on introducing of functional genes into cells by ex vivo or in vivo techniques and which is one of the most important applications of gene transfer; see, e.g., Schaper[73] and references cited therein.

Thus, in a preferred embodiment, the nucleic acid molecule comprised in the pharmaceutical composition for the use of the invention is designed for the expression and secretion of the MCP by cells in vivo in a form suitable for the attraction of monocytes by, for example, direct introduction of said nucleic acid molecule or introduction of a plasmid, a plasmid in liposomes, or a viral vector (e.g. adenoviral, retroviral) containing said nucleic acid molecule.

As discussed above, the growth of arteries from preexisting arteriolar connections is essential for the delivery of nutrition to tumors. Thus, if the growth of said vessels to the tumor would be suppressed suppression and/or inhibition of tumor growth is to be expected. Accordingly, the present invention also relates to a method for the treatment of tumors comprising contacting tissue or cells with an agent which suppresses the growth of collateral arteries and/or other arteries from preexisting arteriolar connections through the attraction of monocytes. Agents which suppress the growth of collateral arteries and/or other arteries from preexisting arteriolar connections may be peptides, proteins, nucleic acids, antibodies, small organic compounds, hormones, neural transmitters, peptidomimics, or PNAs (Milner, Nature Medicine 1 (1995), 879–880; Hupp, Cell 83 (1995), 237–245; Gibbs, Cell 79 (1994), 193–198).

The present invention further relates to the use of an agent which suppresses the growth of collateral arteries and/or other arteries from preexisting arteriolar connections through the attraction of monocytes for the preparation of a pharmaceutical composition for the treatment of tumors.

In a preferred embodiment, the agent used in the methods and uses of the invention as described above inhibits the biological activity of a MCP and/or inhibits an intracellular signal triggered in the monocytes through the receptor for an MCP, preferably the aforementioned agent blocks and interaction of the MCP and its receptor. Various receptors of MCPs are described in the prior art, for example in Charo[68] and Chemokine Receptors[62]. Furthermore, it has recently been shown that phosphorylation of the MCP-receptor mediates receptor desensitization and internalization and that via altering the phosphorylation sites of the receptor the chemotactic response of leukocytes to MCP-1 and related chemokines can be modulated[67].

In another preferred embodiment, said receptor is selected from the group consisting of CCR1, CCR2, CCR4 and CCR5.

In a preferred embodiment, the agent which interaction of the MCP and its receptor is selected from the group consisting of
(i) an anti-MCP antibody and an anti-MCP-receptor antibody; and/or
(ii) a non-stimulatory form of an MCP protein and a soluble form of an MCP-receptor.

Anti-MCP or MCP-receptor antibodies can be prepared by well known methods using the purified MCP or its receptor or parts thereof as an antigen.

Monoclonal antibodies can be prepared, for example, by the techniques as described in Köhler and Milstein, Nature 256 (1975), 495, and Galfré, Meth. Enzymol. 73 (1981), 3, which comprise the fusion of mouse myeloma cells to spleen cells derived from immunized mammals. Furthermore, antibodies or fragments thereof to the aforementioned MCPs or their receptors can be obtained by using methods which are described, e.g., in Harlow and Lane "Antibodies, A Laboratory Manual", CSH Press, Cold Spring Harbour, 1988. These antibodies may be monoclonal antibodies, polyclonal antibodies or synthetic antibodies as well as fragments of antibodies, such as Fab, Fv, or scFv fragments etc.

Non-stimulatory forms of MCPs and antagonists of MCP-receptors have been described, for example, in Gong[65].

In another embodiment, the agent which suppresses the growth of collateral arteries and/or arteriogenesis is an anti-sense RNA of the MCP or of its receptor. It might be desirable to inactivate the expression of the gene encoding the MCP and/or encoding its receptor. This can be achieved by using, for example, nucleic acid molecules which represent or comprise the complementary strand of the mRNA transcript or part thereof encoding the MCP or its receptor. Such molecules may either be DNA or RNA or a hybrid thereof. Furthermore, said nucleic acid molecule may contain, for example, thioester bonds and/or nucleotides analogues, commonly used in oligonucleotide anti-sense approaches. Said modifications may be useful for the stabilization of the nucleic acid molecule against endo- and/or exonucleases in the cell. Said nucleic acid molecules may also be transcribed by an appropriate vector containing a chimeric gene which allows for the transcription of said nucleic acid molecule in the cell. Such nucleic acid molecules may further contain ribozyme sequences which specifically cleave the mRNA encoding the MCP or its receptor. Furthermore, oligonucleotides can be designed which are complementary to a region of the gene encoding the MCP or its receptor (triple helix; see Lee Nucl. Acids Res. 6 (1979), 3073; Cooney, Science 241 (1988), 456 and Dervan, Science 251 (1991), 1360), thereby preventing transcription and the production of the MCP or its receptor.

In a preferred embodiment, the anti-sense RNA is designed to be expressed in vascular cells or cells surrounding preexisting arteriolar connections to a tumor.

In a preferred embodiment, methods and uses of the invention are employed for the treatment of a tumor which is a vascular tumor, preferably selected from the group consisting of Colon Carcinoma, Sarcoma, Carcinoma in the breast, Carcinoma in the head/neck, Mesothelioma, Glioblastoma, Lymphoma and Meningeoma.

In a preferred embodiment, the pharmaceutical composition in the use of the invention is designed for administration by catheter intraarterial, intravenous, intraperitoneal or subcutenous routes. In the examples of the present invention the human form of the MCP-1 protein was administered locally via osmotic minipump. Positive immunohistochemical staining for BrdU infused into two animals via the same route as MCP-1 demonstrated that local delivery of substances into the collateral circulation is feasible.

The said MCP and its encoding nucleic acid molecule may be used for therapeutical purposes in various forms. Either as in the experiments described herein, locally via implanted pumps, or as arterial or venous boluses either systemically or locally via specially designed catheters or other device. They may also be injected intramuscularly or into any other tissues in which collateral artery growth needs to be promoted. Alternatively they can be bound to microcapsules or microspheres before injection.

Another approach would be to use a gene-transfer approach, either using a plasmid, or a plasmid embedded in liposomes, or viral vectors. One may either use an in vivo gene-transfer approach for which multiple devices, like double balloon or other catheters have been designed or via direct injection into the targeted tissue as described above. Alternatively it is possible to use an ex vivo approach isolating cells which are known to lodge in tissues in which vessel growth needs to be promoted or inhibited from the body which are then transfected using one of the above mentioned methods and reinjected.

The use and methods of the invention can be used for the treatment of all kinds of diseases hitherto unknown as being related to or dependent on the modulation of the growth of collateral arteries and/or other arteries from preexisting arteriolar connections. The methods and uses of the present invention may be desirably employed in humans, although animal treatment is also encompassed by the methods and uses described herein.

The figures show

FIG. 1: Monocyte/macrophage accumulation after femoral artery occlusion in the rabbit hindlimb. A) A monocyte adheres to the wall of an excised collateral artery (arrow); two other macrophages staining green (bright) have already penetrated the vessel wall. B) Macrophages are also found interstitially in the lower limb (arrows). C) and D) Monocytes/macrophages staining green (bright) are much more numerous in animals treated with MCP 1 (scale bars: 20 mm).

Figure 2A:
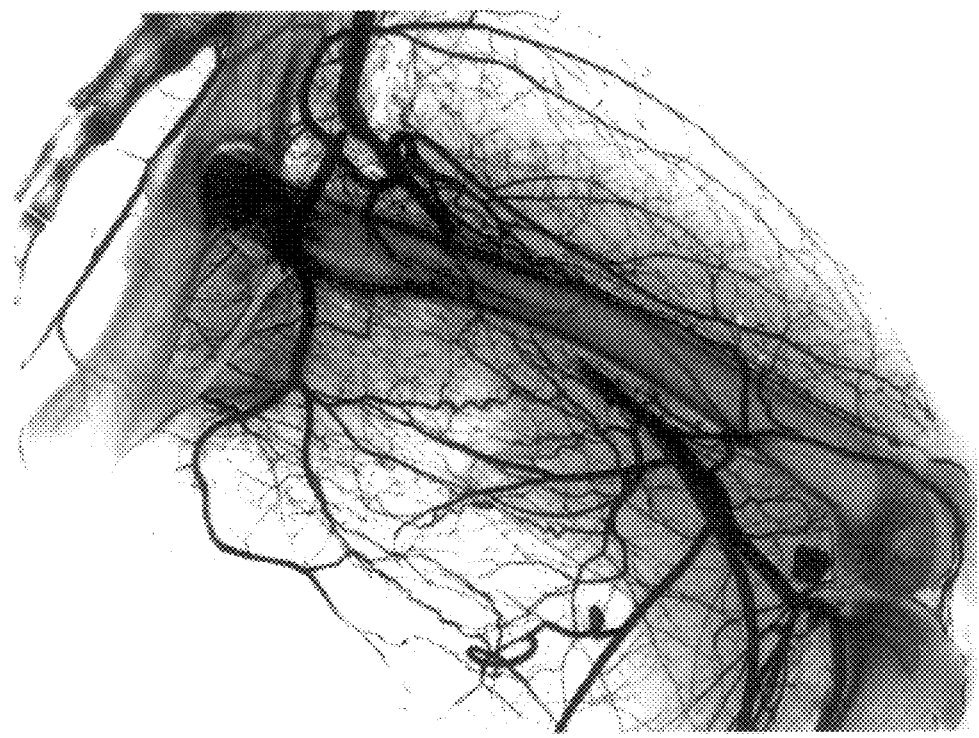
Figure 2B:
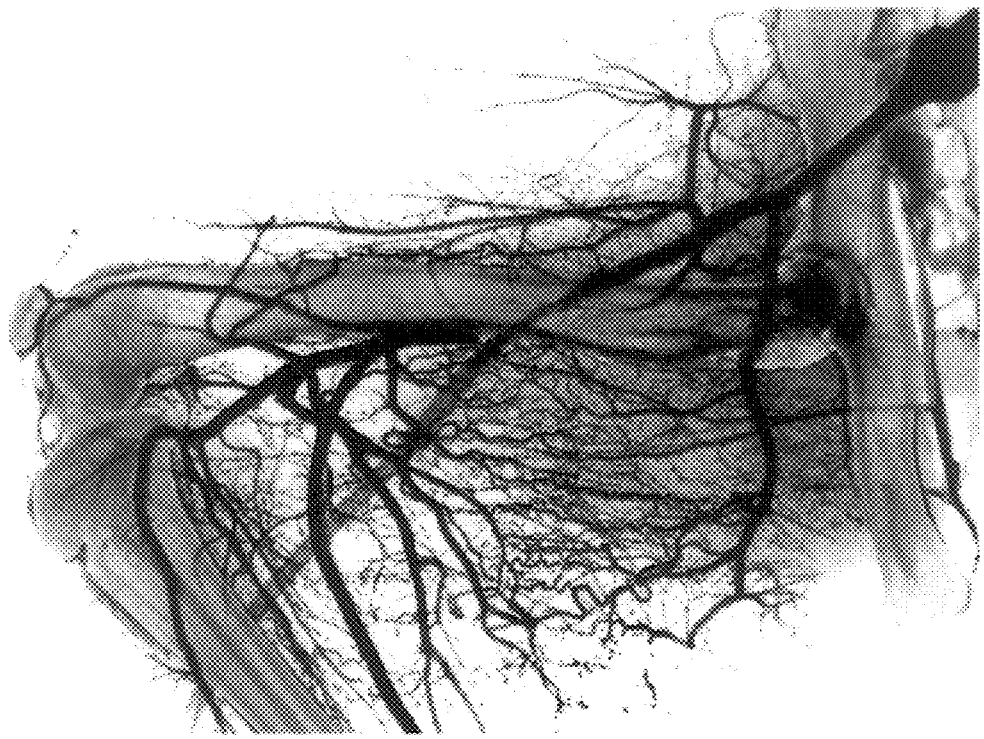

FIG. 2: Post-mortem angiograms of rabbit hindlimbs after one week of femoral artery occlusion. A) Without MCP-1 treatment. B) After one week of local MCP-1 infusion. The density of collateral vessels with typical corkscrew appearance is markedly increased in hindlimbs of animals treated with MCP-1.

FIG. 3 A) Staining of bromodeoxyuridine (BrdU) (green (bright) fluorescence) infused continuously by minipump as proliferation marker and counterstained with phalloidin-TRITC as marker for actin: Pronounced incorporation of BrdU in endothelial and smooth muscle cells during the first week of femoral artery occlusion. B) Specific staining of capillaries with an antibody against CD 31 in a normal gastrocnemial muscle. C) The same muscle stained for CD 31 after one week of occlusion; the number of capillaries has increased. D) Gastrocnemial muscle after one week of occlusion and MCP 1 infusion; capillaries are more numerous after MCP 1 treatment (Scale bars in all pictures: 20 mm).

Figure 4:
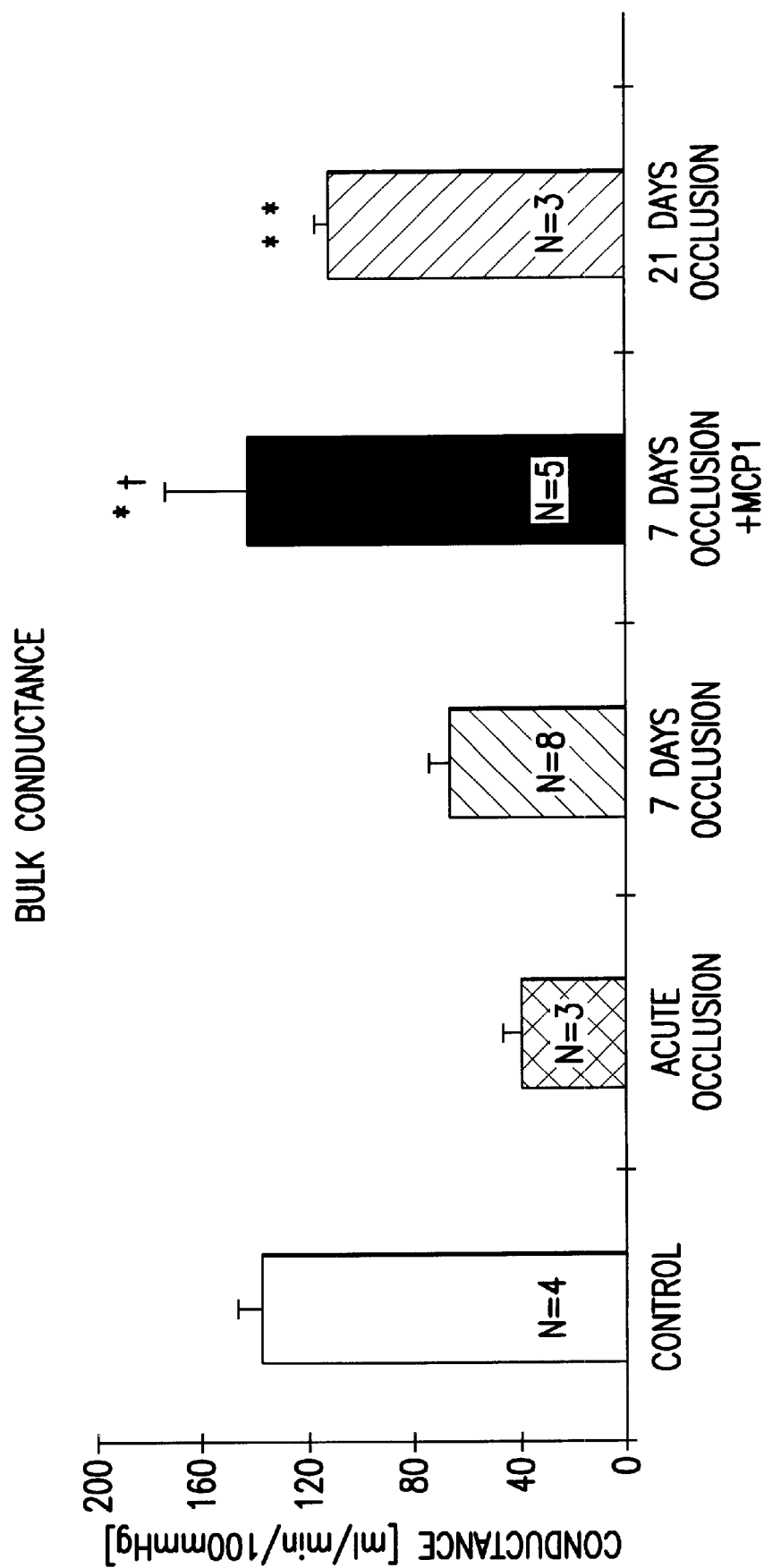

FIG. 4: Bulk conductance of rabbit hindlimbs after one week of femoral artery occlusion with local MCP-1 infusion in comparison to control hindlimbs after acute, one week, 3 weeks or no occlusion. Bulk conductance in animals treated with MCP-1 was significantly higher than in control animals after the same time of femoral artery occlusion and reached values of non occluded legs (*$p<0.05$ and**$p<0.01$ as compared to acute occlusion; †$p<0.05$ as compared to one week of occlusion without MCP-1 treatment).

Figure 5:
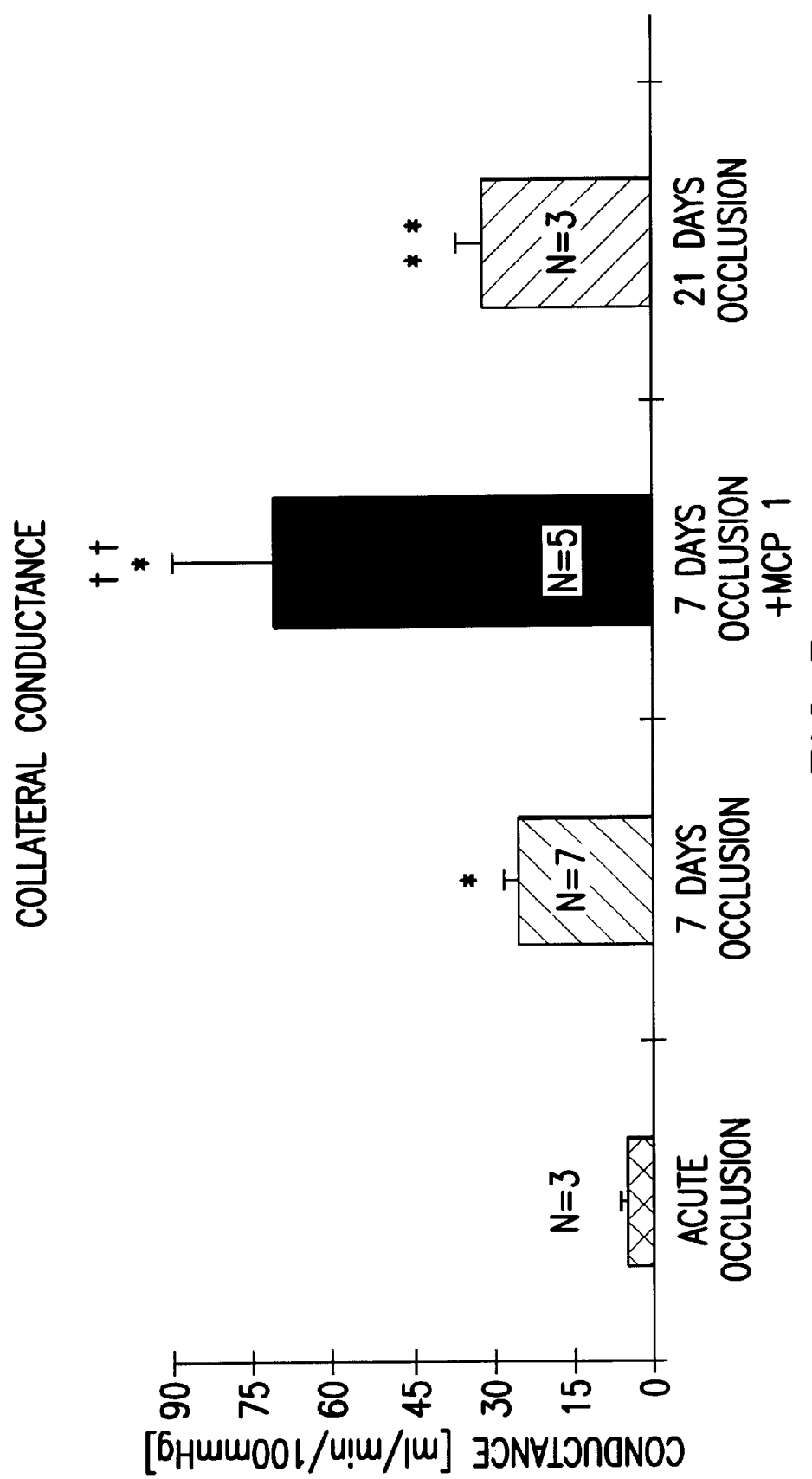

FIG. 5: Collateral conductance of rabbit hindlimbs after one week of femoral artery occlusion with local MCP-1 infusion in comparison to control hindlimbs after acute, one week, and 3 weeks of occlusion in different regions. Collateral conductance in animals treated with MCP-1 was significantly higher than in control animals after the same time of femoral artery occlusion in the quadriceps and adductor longus muscle region. These values tended to be higher than those observed in control animals after three weeks of femoral artery occlusion (*$p<0.05$ and**$p<0.01$ as compared to acute occlusion; ††$p<0.01$ as compared to one week of occlusion without MCP-1 treatment).

Figure 6:
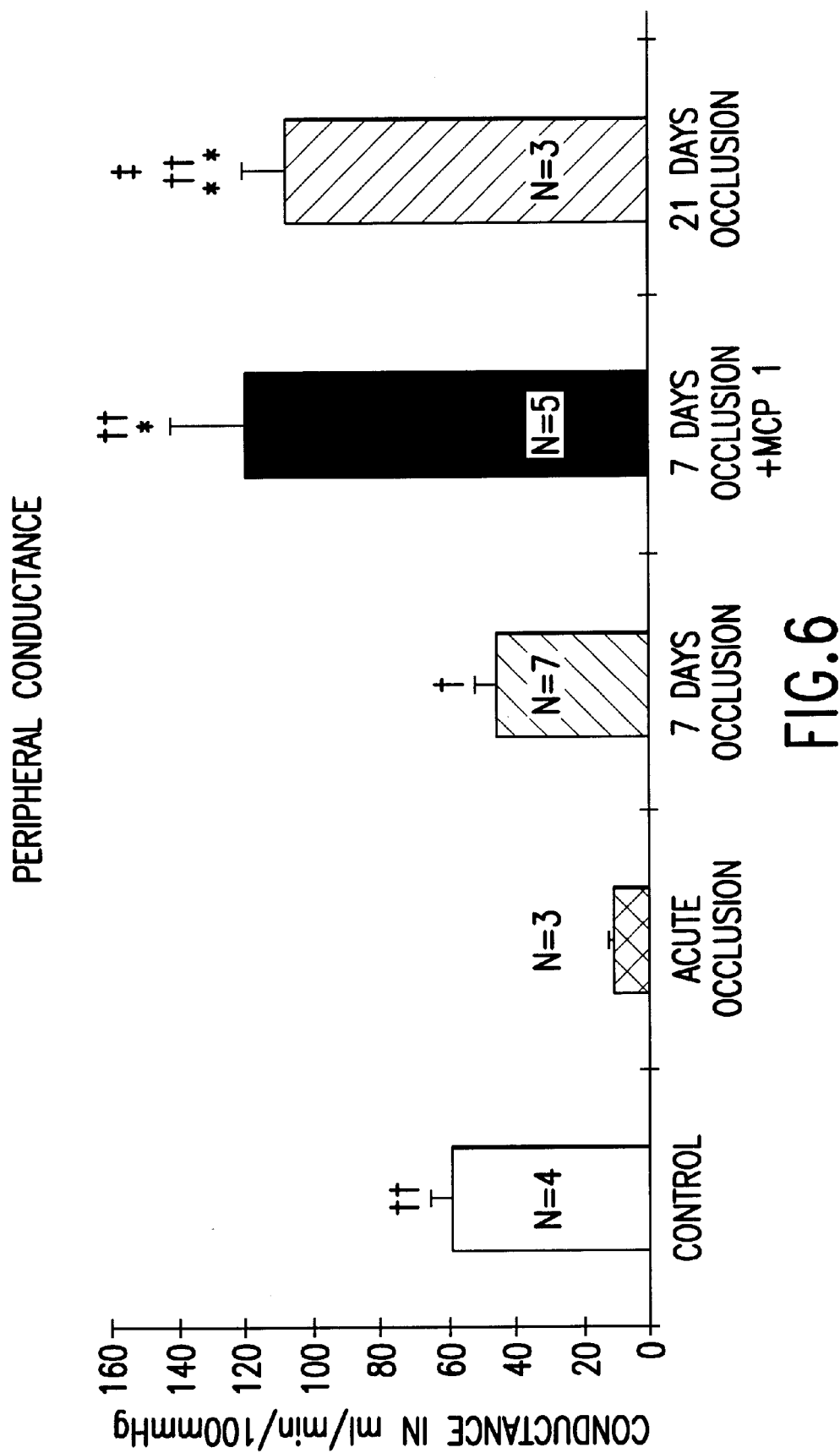

FIG. 6: Peripheral conductance of rabbit hindlimbs after one week of femoral artery occlusion with local MCP-1 infusion in comparison to control hindlimbs after acute, one week and 3 weeks of occlusion. Peripheral conductance in animals treated with MCP-1 was significantly higher than in control animals after the same time of femoral artery occlusion. Similar to collateral conductance these values tended to be higher than those observed in control animals after three weeks of femoral artery occlusion (*$p<0.05$ and**$p<0.01$ as compared to acute occlusion; ††$p<0.01$ as compared to one week of occlusion without MCP-1 treatment).

Figure 7:
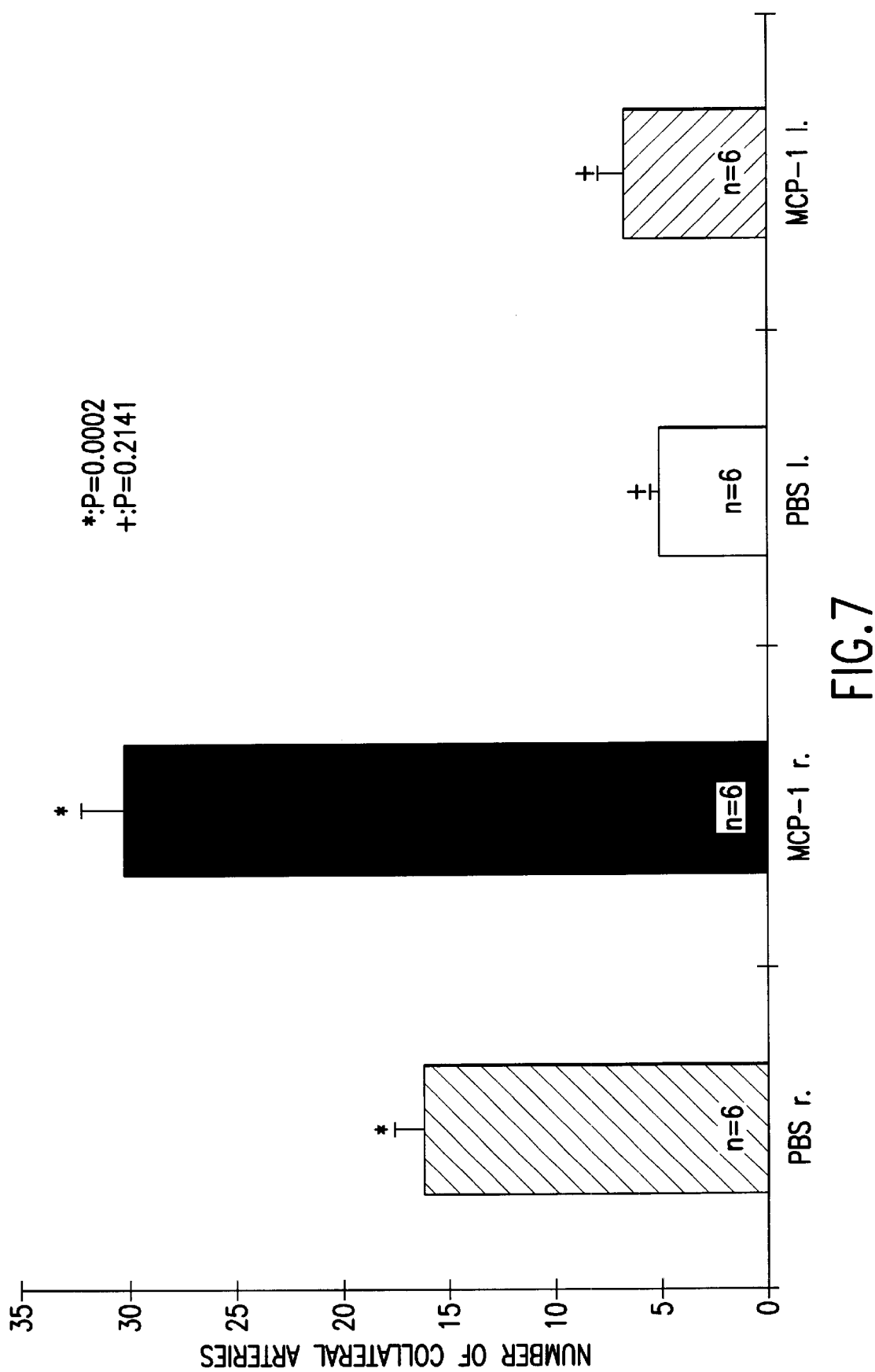

FIG. 7: Number of collateral arteries identified by their stem regions, midzone regions and reentry regions in stereoscopic, 3-dimensional angiograms. The number of collateral arteries after one week of occlusion (right leg) was almost twice as high in animal treated with MCP-1 as compared to animals treated with the carrier alone. No significant differences were found in the non-occluded left control leg.

The examples illustrate the invention.

EXAMPLE 1

Femoral Artery Occlusion of Animals and Local Delivery of Agents

The present study was performed with permission of the State of Hesse, Regierungspräsidium Darmstadt, according to §8 of the German Law for the Protection of Animals. It conforms with the Guide for the Care and Use of Laboratory Animals published by the US National Institutes of Health (NIH Publication No.85-23, revised 1985). Twelve rabbits were subjected to 7 days of bilateral femoral artery occlusion. They were randomly assigned to either receive Monocyte Chemotactic Protein-1 (MCP-1; PeproTech Inc, Rocky Hill, N.J., USA) locally via osmotic minipump (2ML-2 Alza Corp, USA; 3 mg in 2 ml phosphate buffered saline (PBS) at a rate of 10 ml/h), PBS via osmotic minipump or no treatment. Nine additional animals were subjected to either no, acute or 21 days of femoral artery occlusion for comparison. Two animals were supplied with an osmotic minipump (2ML-2 Alza Corp, USA) delivering bromodeoxyuridin (BrdU: Sigma Chemicals, St. Louis) via the same route as MCP-1 to verify the function of the local delivery system and to study the proliferation of collateral arteries and capillaries.

For the initial surgery the animals were anesthetized with an intramuscular injection of ketamin hydrochloride (4–8 mg per kilogram body weight) and xylazin (8–9 mg per kilogram body weight). Supplementary doses of anesthetic (10–20% of the initial dose) were given intravenously as needed. Surgery was performed under sterile conditions. Femoral arteries were exposed and cannulated with a sterile polyethylene catheter (1 mm i.d., 1.5 mm o.d.) pointing upstream with the tip of the catheter positioned distally of the branching of the arteria circumflexa femoris. The catheter itself was connected to the osmotic minipump (2ML-2 Alza Corp, USA) which was implanted under the skin of the lower abdomen. Rabbits were outfitted with a specially designed body suit which allowed them to move freely but prevented selfmutilation. They were housed together in a large cage with free access to water and chow to secure mobility. Before sacrifice the animals received another intramuscular injection of ketamin hydrochloride and xylazin. The animals then underwent tracheostomy and were artificially ventilated. Anesthesia was deepened with pentobarbital (12 mg/Kg bodyweight per hour). The carotid artery was cannulated for continuous pressure monitoring. The arteria saphena magna (anterior tibial artery in humans; main arterial supply to the lower limb and foot in the rabbit) was exposed just above the ankle and cannulated with polyethylene tubing (0.58 mm i.d., 0.96 mm o.d.). They were connected to a Statham P23DC pressure transducer (Statham, Spectramed, USA) for measurement of peripheral pressures. After heparinization with 5000 units of heparin both external iliac arteries were exposed and cannulated with 2.0 mm bore metal tubing. The abdominal circumflex artery and the arteria spermatica were ligated and a tourniquet placed proximally around both thighs leaving the femoral artery patent. The femoral and sciatic vein were incised for drainage of venous blood. The animals then were bled, the legs were amputated above the hip and quickly transferred to the perfusion apparatus. No animal was lost during or after the primary operation. It was also not observed any gangrene or gross impairment of function after femoral artery occlusion. Two animals had to be excluded from the study because of air embolism. After finishing the experiment all fluid remaining in the reservoir of the minipump was collected and weighed. In the two control animals receiving bromodesoxyuridine (BrdU), BrdU staining was performed by standard immunohistochemical methods described elsewhere[26]. Evaluation of fluids remaining in the reservoir revealed that pumping at a rate of 10 ml/h was accomplished in all experiments. Positive immunohistochemical staining for BrdU demonstrated that local infusion into the collateral circulation via osmotic minipump was feasible.

EXAMPLE 2

Ex vivo Pressure-flow Relations

The legs were perfused with autologuous oxygenated blood warmed to 37° C. using a Stoeckert roller pump (Stoeckert GmbH, Germany) and a Jostra M2 membrane oxygenator (Jostra GmbH, Germany). Hematocrit was kept between 34% and 37% and oxygen saturation at 99%. Maximal vasodilation was achieved by adding 25 mg of papaverine (Sigma Chemicals, St. Louis USA) to the perfusate (priming volume: 60 ml). The legs were perfused at three different pressure levels (40, 60 and 80 mmHg). After stabilization radioactive microspheres were injected and a reference sample drawn using a syringe pump (Braun Melsung, Germany). For each pressure level microspheres labeled either with Ruthenium, Cerium and Niobium or Scandium (Dupond NEN Products, USA) were randomly chosen. This allowed to relate tissue perfusion to different perfusion pressures. Total flow was determined using an ultrasonic inline flow probe connected to a T201 flowmeter (Transonic Systems, Inc, USA). Systemic pressures and peripheral capillary pressures were traced with a Statham P23DC pressure transducer (Statham, Spectramed, USA). All recordings were transferred online to a computerized recording system (MacLab, Apple Microsoft USA) from which they were recovered for further processing. Quadriceps, adductor lonaus and adductor magnus, gastrocnemius, soleus and peroneal muscles were dissected from the leg and each muscle was divided into five consecutive samples from the proximal to the distal end. Samples were weighed and subsequently analyzed together with the respective reference samples using a Ge-detector as described previously[27]. Of the total 27 hindlimbs which were perfused 4 were excluded because peripheral pressures could not be obtained and 1 was excluded from the determination of collateral and capillary conductances because of sampling errors. There were no significant differences in conductances between animals receiving PBS via minipump and animals receiving no treatment (bulk conductance: 57.2+/−8.60 vs. 69.2+/−10.01; collateral conductance: 24.5+/−5.69 vs. 25.3+/−3.29; all data in ml/min/100 mmHg). Therefore these two groups were combined in the final analysis.

For the calculation of sample flows mean sample activity per gram of muscle weight ($A_m/g$) was used and related to total flow per gram-of muscle weight ($F_{t/g}$) which allowed the calculation of sample flow ($F_s$) using the equation $F_s = F_t/A_m \times A_s$. This correlated well with the calculation of sample flow ($F_s$) from sample activity ($A_s$), reference sample activity ($A_r$), weight of the reference sample ($W_r$) and time of reference sample withdrawal (t) following the equation $F_s = A_s/A_r \times W_r/t$.

In the present model collateral arteries developing after femoral artery occlusion in typical corkscrew formation supply blood to the distal adductor region and the lower leg. Systemic pressure (SP) and peripheral pressure was used in the saphenous artery (PP). Venous pressure was equal to atmospheric pressure (AP; zero in the present case). Since arterial resistances are much lower than collateral and peripheral resistances they can be neglected. SP represents the pressure at the stem region of the collateral arteries. PP is the pressure at the reenty region and is identical to the pressure head of the circulation in the lower leg, AP the pressure at the venous end of the peripheral circulation. Collateral flow (Fc) is equal to the sum of flow to the tissue of the distal adductor (FdTA) plus the flow to the tissue of the lower leg (FTII). (Flow to the bone was very small and the main arterial supply to the foot was ligated. Therefore these values were neglected in our calculation). Collateral resistance (Rc) was defined as pressure difference between perfusion pressure (SP) and peripheral pressure (PP) divided by the flow going to the distal adductor and the lower leg. Peripheral resistance (Rp) was defined as peripheral pressure (PP) divided by flow to the lower leg (FTII) and bulk conductance was defined as systemic pressure (SP) divided by bulk flow recorded with the ultrasonic flow probe. The reciprocal values of these resistances represent collateral-, peripheral- and bulk conductance (Cc, Cp and Cb) Because a positive pressure intercept is observed even at maximal vasodilation all conductances were calculated from the slope of pressure flow relations.

After one week of femoral artery occlusion bulk conductance as calculated from pressure flow relations was significantly higher in animals treated with MCP-1 (142.1+/−31.71 ml/min/100 mmHg versus 66.2+/−7.76 ml/min/100 mmHg; $p<0.05$)(FIG. 4). After seven days of occlusion bulk conductances of MCP-1 treated animals reached levels even higher than in untreated animals after three weeks of femoral artery occlusion and was comparable to values in non-occluded hindlimbs.

Collateral conductance also was significantly higher after one week of occlusion in animals treated with MCP1 as compared to animals without this treatment (70.6+/−19.23 ml/min/100 mmHg versus 25.1+/−2.59 ml/min/100 mmHg; $p<0.01$)(FIG. 5). Collateral conductance of animals that had received MCP-1 for one week tended to be even larger than in untreated animals after three weeks of femoral artery occlusion in all areas in which collateral growth was observed. Conductance in the calf also was significantly higher after one week of femoral artery occlusion in animals with MCP-1 treatment as compared to rabbits which had not received MCP-1 (119.3+/−22.37 ml/min/100 mmHg versus 45.4+/−6.80 ml/min/100 mmHg; $p<0.01$) (FIG. 6). All data are presented as mean +/–SEM. Intergroup comparisons were performed by unpaired Student's t-test. In the case of unequal variances the Mann-Whitney Rank Sum test was used. Probability values of 0.05 or less were required for assumption of statistical significance.

Treatment with MCP-1 increased both collateral and peripheral conductance 2-fold as compared to untreated animals after 7 days of femoral artery occlusion. Thus animals locally injected with MCP-1 reached normal conductance values after one week of occlusion whereas conductance values in untreated animals did not return to normal levels even three weeks after occlusion. As mentioned above MCP-1 is mainly known as chemoattractant for monocytes[31,35]. One possible explanation would therefore be that MCP-1 exerts its pronounced effects on collateral- and peripheral conductance via attraction and activation of monocytes that in turn produce growth factors which lead to the proliferation of endothelial and smooth muscle cells. This requires that monocytes adhere to the small arteriolar connections which are very likely the origin of our collateral arteries[35,48,49]. These preexisting arteriolar connections experience a large increase in shear stress when the main arterial supply to the lower leg is occluded.

EXAMPLE 3

Post Mortem Angiography

After maximal vasodilatation legs were warmed to 37° C. and perfused with Krebs-Henseleit buffered saline for one minute followed by perfusion with contrast medium based on bismuth and gelatine according to a formula developed by Fulton[28]. Subsequently the contrast medium was allowed to gel by placing the limb on crushed ice and angiograms were taken at two different angles in a Balteau radiography apparatus (Machlett laboratories, USA) using a single enveloped Structurix D7 DW film (AGVA, Germany). The resulting stereoscopic pictures allowed analysis of collateral growth in three dimensions.

Post mortem angiograms exhibited corkscrew collaterals mainly in the adductor longus, adductor magnus and vastus intermedius muscles connecting the perfusion bed of the arteria femoralis profunda to that of the arteria saphena parva in the adductor muscles and the perfusion bed of the arteria circumflexa femoris lateralis to that of the arteriae genuales in the quadriceps muscle. Angiograms taken from hindlimbs of animals with MCP-1 treatment showed a remarkable increase in the density of these collateral vessels (FIG. 2 A and B). No collateral vessels were visible on angiograms in the lower limb of normal and MCP-1 treated animals.

EXAMPLE 4

Histological Studies

The abdominal aorta was cannulated with a 2 mm bore metal cannula, the chest was opened and the heart exposed. After incision of the right atrium to allow drainage of rinsing solution and fixative perfusion was started with a rinsing solution containing 0,5% BSA, 5 mM EDTA, 0.317 mg/l Adenosin in phosphate buffered saline (PBS)×1.5 for 5 min followed by fixation with formalin 4% in the rinsing solution without BSA for 20 min. Subsequently a post mortem angiography was performed as described in Example 3. This allowed the precise localization and excision of collateral vessels, their stem and reentry regions.

Figure 1C:
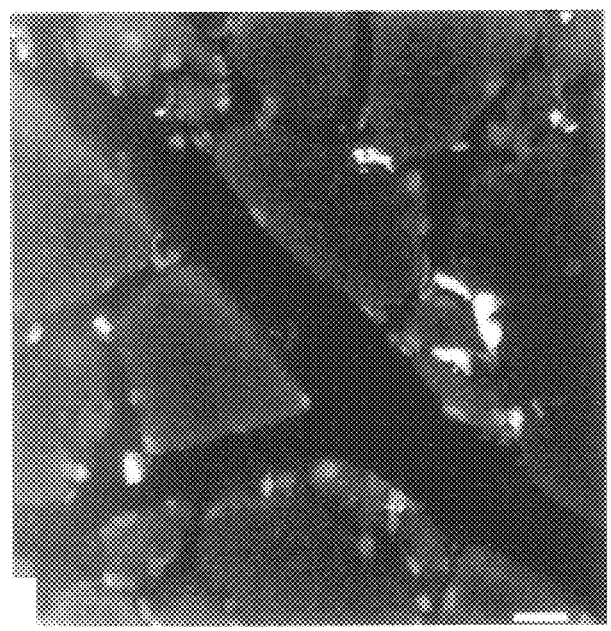
Figure 1D:
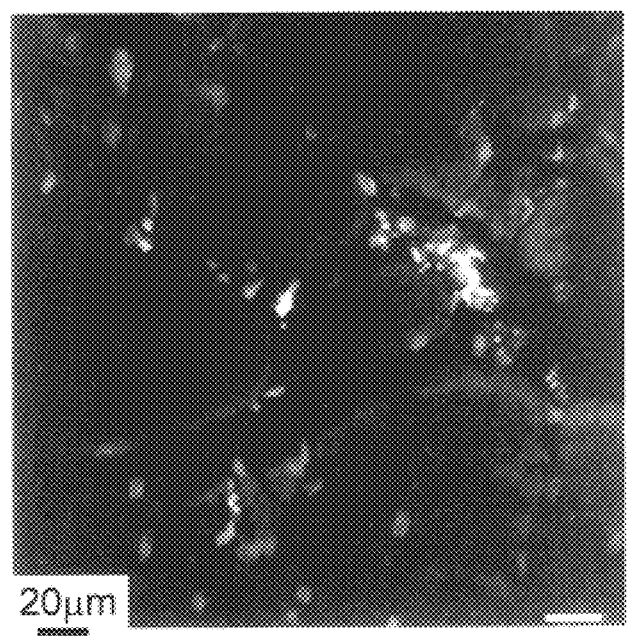

For immunohistological studies, samples were kept in 20% saccharose overnight and then frozen and mounted on cork in nitrogen cooled methylbutane at –130° C. They were stored at –80° C. until further processing. For visualization of BrdU cryostat sections of 20 mm were obtained in a Leica CM 3000 cryotom, mounted onto silicone coated slides and incubated in 2 mol/l HCl at 38° C. for 20 minutes. After rinsing in PBS 3 times for 5 minutes they were incubated with the primary antibody against BrdU (Clone BU20a, DAKO Corp.), 1:20 in PBS at 4° C. overnight. For detection the samples were incubated with a biotinylated donkey antimouse antibody (DIANOVA Corp) 1:100 in PBS for one hour followed by incubation with streptavidin-cy2 (Biotrend, Koeln, Germany) 1:100 in PBS for 30 minutes. Finally sections were counterstained either with 7-aminoactinomycin D (7-AAD 1:50 in PBS, Molecular Probes, Eugene, Oregon USA) as nuclear stain or phalloidin-TRTC (1:100 in PBS) as marker for actin. Slides were mounted in Mowiol (Hoechst, Frankfurt/M, Germany) and viewed by Leica confocal laser microscope. Neighboring sections treated identically but omitting the primary antibody served as a negative control. Immunohistochemical staining of capillary endothelial cells was performed following the protocol described above but with an antibody against CD 31 (DACO, Germany), an endothelial specific antigen, as primary antibody. Staining for macrophages was performed using RAM 11 (DACO, Germany), a specific antibody against rabbit macrophages as primary antibody. After femoral artery occlusion monocytes/macrophages were found to accumulate in vessel walls of excised collateral arteries and intersitially in the lower limb (FIGS. 1A and B). They were more numerous in animals treated with MCP-1 (FIGS. 1C and D). Furthermore white plaques were seen macrospically around the infusion site in all animals receiving MCP-1. These plaques contained large numbers of mononuclear cells which predominantly were identified as monocytes/macrophages by immunohistochemical staining with Ram 11 (Dako GmbH, Hamburg, Germany). By macroscopical inspection of the injection site and histological examination of collateral arteries from the thigh and tissue sections from calf muscles it became evident that MCP-1 injection had led to an increase of monocyte accumulation in our experiment. Positive staining of excised collateral arteries for BrdU provided evidence that collateral vessels observed on angiography in the thigh were truly proliferating.

Figure 3A:
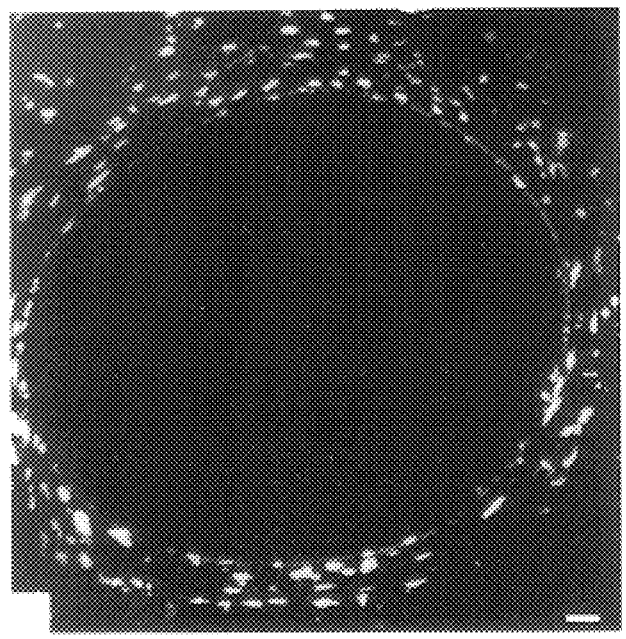
Figure 3B:
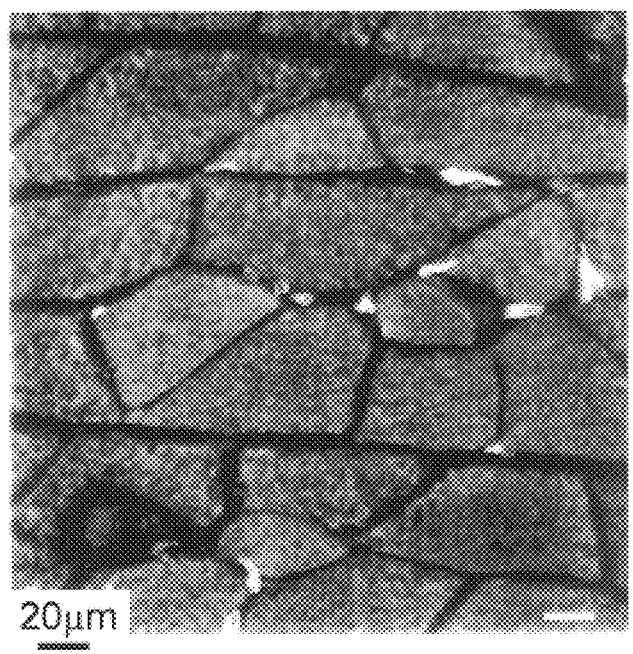
Figure 3C:
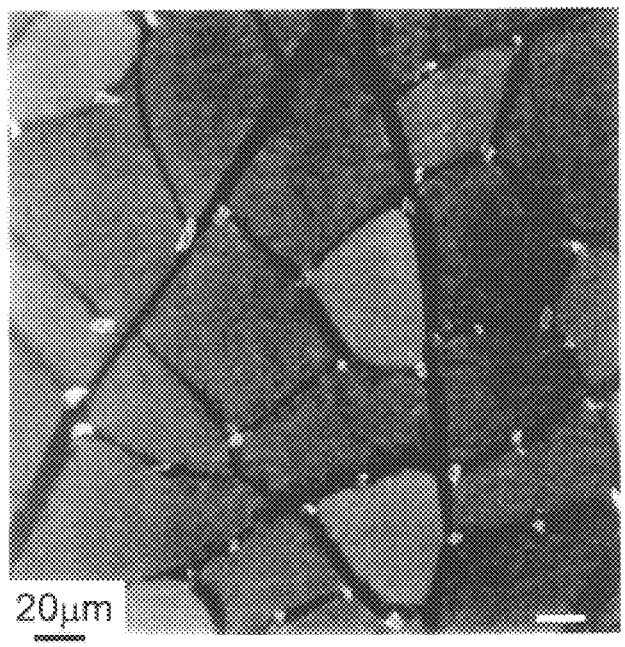
Figure 3D:
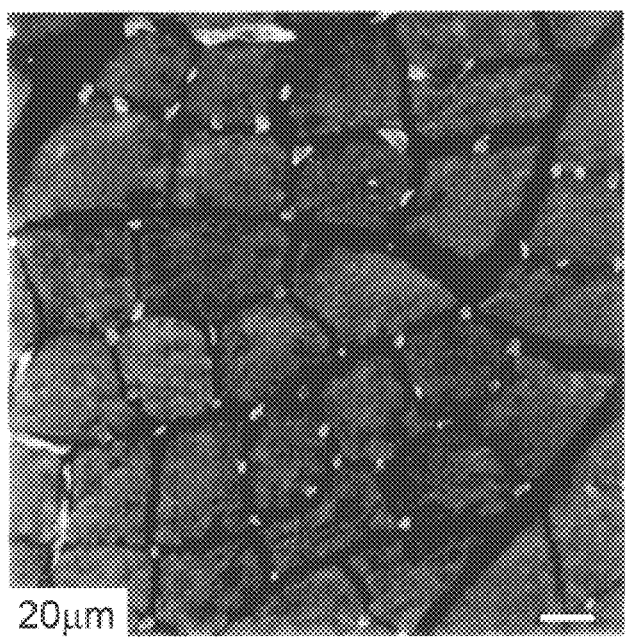

Collateral arteries excised after 7 days of occlusion showed proliferation of endothelial- and smooth muscle cells on BrdU staining (FIG. 3A). Proliferation of capillary endothelial cells was seen in the lower limb leading to an increase in the number of capillaries 7 days after occlusion (Control leg: FIG. 3B; leg after 7 days of occlusion: FIG. 3 C). MCP 1 treated animals showed more capillaries in the lower limb than untreated animals after a week of occlusion indicating enhancement of capillary sprouting by MCP 1 (FIG. 3D).

The immunohistochemical studies after continuous BrdU infusion clearly demonstrated that collateral vessel formation in the thigh involved proliferation of endothelial- and smooth muscle cells, given the fact that the normal generation time for endothelial cells and similar for smooth muscle cells is at least six months and proliferation is usually not seen in normal arteries[39]. The degree of proliferation is similar to that of collateral arteries in the dog heart after ameroid constrictor placement and approaches that of tumors[40]. Although this does not exclude the possibility that MCP-1 enhances collateral artery proliferation via hypothetical, unrecognized chronic vasodilatory effects, the rapidity and magnitude of the increase in collateral conductance is far higher than with any other known vasodilator[41-44]. Furthermore monocytes have been shown to downregulate nitric oxide synthase, a very potent vasodilator, in cultured aortic endothelial cells suggesting that MCP-1 would rather inhibit than enhance vasodilation[45]. Therefore vasodilation is a very unlikely explanation for the above findings. The higher density of collateral arteries on the angiograms further supports the notion that collateral artery growth is responsible for the increase in collateral conductance.

In contrast to the thigh were the density of collateral arteries increased, more capillaries were found in histological sections from calf muscles of MCP-1 treated animals as compared to control animals after seven days of occlusion. An antibody against CD31(PECAM) was chosen as marker for endothelial cells because this cell adhesion molecule is constitutively expressed on all endothelial cells and not dependent on their phenotype or activation[46,47]. Using BrdU as a marker for proliferation only proliferating capillaries in the calf muscles were detected. No other vessel type was found to grow in this region. As for collateral conductance passive vessel enlargement due to vasodilation can be excluded as a reason for peripheral conductance changes by performing the measurements at maximal vasodilatation. Thus changes in peripheral conductance are most likely attributable to capillary sprouting.

The histological data suggests that more monocytes accumulate in MCP-1 treated animals. Since monocytes are potentially capable of producing large amounts of growth factors this further supports the hypothesis that monocytes are the mediator of the changes seen with MCP-1 treatment.

In summary, our results have shown that local infusion of MCP-1, a potent and specific chemoattractant for monocytes, is able to markedly increase collateral- as well as peripheral conductance. Angiographic and histological findings indicate that this effect is due to augmented collateral artery- and capillary proliferation and suggest that adhesion, activation and migration of monocytes play an important role in both types of vessel growth.

EXAMPLE 5

Number of Collateral Arteries

Post-mortem angiographies were obtained as described in Example 3. For quantification the bone was extracted and the thigh muscles were unfolded before placing the tissue in the Balteau radiography apparatus. This allowed the identification and counting of individual collateral arteries by virtue of their stem regions, midzone regions and reentry regions on stereoscopic angiograms. The number of collateral arteries thus counted did not differ in individual animals when obtained independently by four different observers. Angiograms were obtained from six animals receiving MCP-1 locally via osmotic minipump after unilateral femoral artery occlusion and compared to angiograms of six animals receiving the carrier PBS via the same route after femoral artery occlusion. The results are shown in FIG. 7.

After seven days of occlusion the number of collateral arteries was almost twice as high in animals receiving MCP-1 as compared to animals receiving PBS alone (30.17+/−1.96 vs 16.17+/−1.4; P<0.001); see Table 1.

TABLE 1

| PBS l. | 5.00 ± 0.45 |
|---|---|
| MCP-1 l. | 6.67 ± 1.17 |
| PBS r. | 16.17 ± 1.40 |
| MCP-1 r. | 30.17 ± 1.96 |
| PBS r. vs. MCP-1 r. | P = 0.0002 |

Table 1: Number of collateral arteries identified by their stem regions, midzone regions and reentry regions in stereoscopic, 3-dimensional angiograms. The number of collateral arteries after one week of occlusion (right leg) was almost twice as high in animal treated with MCP-1 as compared to animals treated with the carrier alone. No significant differences were found in the non-occluded left control legs. There was no difference in the number of collateral arteries between MCP-1- and carrier-treated animals in the non-occluded control legs suggesting that additional mechanisms are necessary in order to promote collateral growth which are elicited by occlusions. MCP-1 therefore will not enhance collateral growth or growth of other vessels in sites without vessel occlusions.

EXAMPLE 6

Long-term Effects of MCP-1 Treatment as Seen by MRI Scanning

Six animals treated with MCP-1 and 6 control animals were investigated with MRI-scanning acutely after 7 days, 2 weeks, 1, 2 and 3 months after unilateral femoral artery occlusion. The anatomical structure was analyzed with high-resolution T1-SE Images. MR-angiography was performed with a 3-D FISP Sequence. Perfusion was measured after an intravenous bolus of GD-DTPA with a TFL-SR-Sequence. Analysis was performed according to the different muscle groups. The number of collateral arteries in MCP-1 treated animals was higher throughout the investigated time frame. In contrast to control animals retrograde filing of the femoral artery was already normalized after 2 weeks of occlusion in MCP-1 treated animals.

REFERENCES

1. Schaper, Schaper, J. Collateral Circulation—Heart, Brain, Kidney, Limbs. Boston, Dordrecht, London: Kluwer Academic Publishers; 1993.
2. Tuder, Flook, Voelkel, J. Clin. Invest. 95 (1995), 1798–1807.
3. Plate, Breier, Weich, Risau, Nature 359 (1992), 845–848.
4. Ferrara, Houck, Jakeman, Leung, Endocrine Reviews 13 (1992), 18–42.
5. Klagsbrun, D'Amore, Annu. Rev. Physiol. 53 (1991), 217–239.
6. Leung, Cachianes, Kuang, Goeddel, Ferrara, Science 246 (1990), 1306–1309.
7. Takeshita, Zheng, Brogi, Kearney, Pu, Bunting, Ferrara, Symes; Isner, J. Clin. Invest. 93 (1994), 662–670.
8. Bauters, Asahara, Zheng, Takeshita, Bunting, Ferrara, Symes, Isner rabbit, Am. J. Physiol. 267 (1994), H1263–H1271.
9. Jakeman, Bennett, Altar, Ferrara, J. Clin. Invest. 89 (1992), 244–253.
10. Peters, Vries, Williams, Proc. Natl. Acad. Sci. 90 (1993), 8915–8919.
11. Millauer, Wizigmann-Voos, Schnürch, Martinez, Möller, Risau, Ullrich, Cell 72 (1993), 835–846.
12. Pasyk, Schaper, Schaper, Pasyk, Miskiewicz, Steinseifer, Am. J. Physiol. 242 (1982), H1031–H1037.

13. Folkman, Tumor angiogenesis. Philadelphia: W. B. Saunders; 1995.
14. Görge, Schmidt, Ito, Pantely, Schaper, Basic Res. Cardiol. 84 (1989), 524–535.
15. Paskins-Hurlburt, Hollenberg, Circ. Res. 70 (1992), 546–553.
16. Shyy, Hsieh, Usami, Chien, Proc. Natl. Adac. Sci. USA 91 (1994), 4678–4682.
17. Wang, Wung, Shyy, Lin, Chao, Usami, Chien, Circ. Res. 77 (1995), 294–302.
18. Wung, Cheng, Chao, Lin, Shyy, Wang, Am. J. Physiol. 270 (1996), H1462–H1468.
19. Schaper, Koenig, Franz, Schaper, Virchows Arch. A. (Pathol Anat) 370 (1976), 193–205.
20. Arras, Mohri, Sack, Schwarz, Schaper, Schaper, Circulation 86 (1992) (Suppl. 1), 0129 (abstr.).
21. Zimmermann, Weihrauch, Schaper, Kluge, Mohri, Arras, Strasser, Schaper, Circulation 88 (1993) (Suppl), 2936 (abstr).
22. Ware, Simons Nature Medicine 3 (1997), 158-164.
23. Jain, Koenig, Dellian, Fukumura, Munn, Melder, Cancer & Metastasis Reviews 15 (1996), 195–204.
24. Adams, Lloyd, Lances 349 (1997), 490–495.
25. Unthank, Fath, Burkhart, Miller, Dalsing, Circ. Res. 79 (1996), 1015–1023.
26. Tanaka, Swanson, Sukhova, Schoen, Libby, Am. J. Pathol. 147 (1995), 617–625.
27. Winkler, Techniques in the Life Sciences. Leeds, U.K.: Elsevier Scientific Publishers Ireland Ltd.; (1984): P316/1–P316/36.
28. Fulton, The Coronary Arteries. Springfield, Ill.: Charles C Thomas; 1965.
29. Kuratsu, Leonard, Yoshimnura, J. Natl. Cancer Inst. 81 (1989), 347–351.
30. Yoshimura, Yuhki, Moore, FEBS Lett. 244 (1989), 487–493.
31. Leonard, Yoshimura, Immunol. Today 11 (1990), 97–101.
32. Cushing, Berliner, Valente, Territo, Navab, Parhami, Gerrity, Schwartz, Forgelman, Proc. Natl. Acad. Sci. USA 87 (1990), 5134–5138.
33. Franci, Wong, Van Damme, Proost, Charo, J. Immunol. 154 (1995), 6511–6517.
34. Garcia-Zepeda, Combadiere, Rothenberg, Sarafi, Lavigne, Hamid, Murphy, Luster, J. Immunol. 157 (1996), 5613–5626.
35. Springer, Ann. Rev. Physiol. 57 (1995), 827–872.
36. Satriano, Shuldiner, Hora, Xing, Shan, Schlondorff, J. Clin. Invest. 92 (1993), 1564–1571.
37. Kumar, Ballantyne, Michael, Kukielka, Youker, Lindsey, Hawkins, Birdsall, Mackay, LaRosa, Rossen, Smith, Entman, Circulation 95 (1997), 693–700.
38. Gorski, Hood, Terjung, Am. J. Physiol. 250 (1986), E441–E448.
39. Schaper, The Collateral Circulation of the Heart. Amsterdam London: Elsevier North Holland Publishing Company; 1971.
40. Schaper, DeBrabander, Lewi, Circ. Res. 28 (1971), 671–679.
41. Matttfeld, Mall, Cardiovasc. Res. 17 (1983), 229–237.
42. Tomling, Acta Pathol. Microbiol. Immunol. Scand. 278 (suppl) (1982), 1–63.
43. Torry, O'Brien, Connell, Tomanek, Am. J. Physiol. 262 (1992), H980–H986.
44. Symons, Firoozmand, Longhurst, Circ. Res. 73 (1993), 503–513.
45. Marczin, Antonov, Papapetropoulos, Munn, Virmani, Kolodgie, Gerrity, Catravas, Arterioscler. Thromb. Vasc. Biol. 16 (1996), 1095–1103.
46. Page, Rose, Yacoub, Pigott, American Journal of Pathology 141 (1992), 673–683.
47. Gräfe, Graf, Auch-Schwelk, Terbeek, Hertel, Fleck, European Heart Journal. 14 (1993), 74–81.
48. Imhof, Dunon, Adv. Immunol. 58 (1995), 345–416.
49. Butcher, Cell 67 (1991), 1033–1036.
50. Luscinskas, Ding, Tan, Dumming, Tedder, Gerritsen, J. Immunol. 156 (1996), 326–335.
51. Resnick, Gimbrone, FASEB J. 9 (1995), 874–882.
52. Tsuboi, Ando, Korenaga, Takada, Kamiya, Biochem. Biophys. Res. Commun. 206 (1995), 988–996.
53. Sampath, Kukielka, Smith, Eskin, McIntire, Annals of Biomedical Engineering 23 (1995), 247–256.
54. Patrick, McIntire, Blood Purif. 13 (1995), 112–124.
55. Ando, Tsuboi, Korenga, Takada, Toyama-Sorimachi, Miyasaka, Kamiya, Am. J. Physiol. 36 (1994), C679–C687.
56. Tsao, Buitrago, Chan, Cooke, Circulation 94 (1996), 1682–1689.
57. Walpola, Gotlieb, Langille, Am. J. Pathol. 142 (1993), 1392–1400.
58. Cybulsky, Gimbrone, Science 251 (1991), 788–791.
59. Kling, Fingerle, Harlan, Lobb, Lang, Circ. Res. 77 (1995), 1121–1128.
60. Majano, Joris, Am. J. Pathol. 146 (1995), 3–15.
61. Reed, J. Cell. Biol. 124 (1994), 1–6.
62. Chemokine Receptors. Immunology Today (1996), Suppl S: 26–27.
63. Kitaura, Nakajima, Ima, Harada, Combadiere, Tiffany, Murphy, Yoshie, J. Biol. Chem. 271 (1996), 7725–7730.
64. Ponath, Quin, Post, Wang, Wu, Gerard, Newman, Gerard, Mackay, J. Exp. Med. 183 (1996), 2437–2448.
65. Gong, and Clark-Lewis, J. Exp. Med. 181 (1995), 631–640.
66. Lusti-Narasimhan., Power, Allet, Alouani, Bacon, Mermod, Proudfoot, Wells, J. Biol. Chem. 270 (1995), 2716–2721.
67. Franci, Gosling, Tsou, Coughlin and Charo, J. Immunology 157 (1996), 5606–5612
68. Charo, Myers, Herman, Franci, Connolly and Coughlin, Proc. Natl. Acad. Sci. USA 91 (1994), 2752–2756
69. Proösl, Van Leuven, Wuyrs, Ebberink, Opdenakker and Van Damme, Cytokine. In press
70. Dahinden, Geiser, Brunner, von Tschamer, Caput, Ferrara, Minry and Baggiolini, J. Exp. Med. 179 (1994), 751
71. Alam, Forsythe, Stafford, Heinrich, Bravo, Proösl and Van Damme, J. Immunol. 153 (1994), 2155
72. Oppenheim, Zachariao, Mukaida and Matsushima, Annu. Rev. Immunol. 9 (1981), 617–648
73. Schaper and Ito, Current Opinion in Biotechnology 7 (1996), 635–640

What is claimed is:

1. A method for enhancing the growth of collateral arteries and/or other arteries from preexisting arteriolar connections in a patient with an occlusive disease, comprising administering to the patient an effective amount of a monocyte chemotactic protein selected from the group consisting of Monocyte Chemotactic Protein-1 (MCP-1), Monocyte Chemotactic Protein-2 (MCP-2), Monocyte Chemotactic Protein-3 (MCP-3), Monocyte Chemotactic Protein-4 (MCP-4), Macrophage Inflammatory Protein-1α (MIP-1α), Regulated upon Activation Normal T cell Expressed and Secreted chemokine (RANTES), CC-chemokine I-309, complement fragment C5a, and platelet-activating factor; thereby enhancing the growth of said arteries of the patient.

2. The method of claim 1, wherein the monocyte chemotactic protein is MCP-1.

3. The method of claim 1, wherein the monocyte chemotactic protein is MCP-2.

4. The method of claim 1, wherein the monocyte chemotactic protein is MCP-3.

5. The method of claim 1, wherein the monocyte chemotactic protein is MCP-4.

6. The method of claim 1, wherein the occlusive disease is an arterial occlusive disease selected from the group consisting of: coronary artery diseases, peripheral occlusive diseases, visceral occlusive diseases, renal artery diseases, and mesenterial arterial insufficiency.

7. The method of claim 6, wherein the arterial occlusive disease is a peripheral occlusive disease.

8. The method of claim 6, wherein the arterial occlusive disease is a coronary artery disease.

9. The method of claim 1, wherein the patient is treated during or after exposure to an agent, radiation or surgical treatment which damages or destroys arteries.

10. The method of claim 1, wherein the monocyte chemotactic protein is a recombinant monocyte chemotactic protein.

11. A method for enhancing the growth of collateral arteries and/or other arteries from preexisting arteriolar connections in a patient with a peripheral occlusive disease, comprising administering to the patient an effective amount of Monocyte Chemotactic Protein-1 (MCP-1), thereby enhancing the growth of said arteries of the patient.

12. The method of claim 11, wherein the MCP-1 is a recombinant MCP-1.

13. A method for enhancing the growth of collateral arteries and/or other arteries from preexisting arteriolar connections in a patient with a coronary artery disease, comprising administering to the patient an effective amount of Monocyte Chemotactic Protein-1 (MCP-1), thereby enhancing the growth of said arteries of the patient.

14. The method of claim 13, wherein the MCP-1 is a recombinant MCP-1.

* * * * *